United States Patent
Gomez et al.

(10) Patent No.: US 12,257,011 B2
(45) Date of Patent: Mar. 25, 2025

(54) ASSOCIATION PROCESSES AND RELATED SYSTEMS FOR MANIPULATORS

(71) Applicant: INTUITIVE SURGICAL OPERATIONS, INC., Sunnyvale, CA (US)

(72) Inventors: Daniel H. Gomez, Los Gatos, CA (US); Ian E. McDowall, Woodside, CA (US); Govinda Payyavula, Sunnyvale, CA (US); John Ryan Steger, Los Gatos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 18/640,936

(22) Filed: Apr. 19, 2024

(65) Prior Publication Data
US 2024/0268905 A1 Aug. 15, 2024

Related U.S. Application Data

(63) Continuation of application No. 17/649,721, filed on Feb. 2, 2022, now Pat. No. 11,986,259, which is a (Continued)

(51) Int. Cl.
*A61B 34/30* (2016.01)
*A61B 17/00* (2006.01)
(Continued)

(52) U.S. Cl.
CPC ............ *A61B 34/30* (2016.02); *A61B 90/361* (2016.02); *G16H 40/60* (2018.01); *A61B 2017/00199* (2013.01); *A61B 2090/365* (2016.02)

(58) Field of Classification Search
CPC .... A61B 2034/2048; A61B 2034/2059; A61B 2034/742; A61B 2090/065;
(Continued)

(56) References Cited

U.S. PATENT DOCUMENTS 6,459,926 B1 10/2002 Nowlin et al.
11,272,993 B2 3/2022 Gomez et al.
(Continued)

FOREIGN PATENT DOCUMENTS

GB 2560390 A 9/2018
WO WO-2011143338 A1 11/2011
WO WO-2014151621 A1 9/2014

OTHER PUBLICATIONS

Anonymous: "GazePointer download|SourceForge.net," Nov. 2016, pp. 3 Pages, XP093085718, Retrieved from the Internet: URL:https://web.archive.org/web/20161111072632/https://sourceforge.net/projects/gazepointer/.
(Continued)

*Primary Examiner* — Scott Luan
(74) *Attorney, Agent, or Firm* — MARSHALL, GERSTEIN & BORUN LLP

(57) ABSTRACT

A computer-assisted medical system includes manipulators, a user input system, a user output system comprising a display device, and a controller configured to execute instructions to perform operations. The operations include, in a pairing mode and in response to a first set of signals generated by the user input system, causing a virtual selector shown on the display device to move relative to an imagery shown on the display device. The operations further include, in the pairing mode, associating a first manipulator with a portion of the user input system based on movement of the virtual selector relative to a represented location of the first instrument, and, in a following mode, controlling motion of the first instrument in accordance to a second set of signals
(Continued)

generated by the user input system in response to operation of the portion of the user input system by a user.

20 Claims, 17 Drawing Sheets

Related U.S. Application Data continuation of application No. 16/633,517, filed as application No. PCT/US2018/042690 on Jul. 18, 2018, now Pat. No. 11,272,993.

(60) Provisional application No. 62/551,702, filed on Aug. 29, 2017, provisional application No. 62/537,795, filed on Jul. 27, 2017.

(51) Int. Cl.
   *A61B 90/00* (2016.01)
   *G16H 40/60* (2018.01)
(58) Field of Classification Search
   CPC ... A61B 2090/571; A61B 34/20; A61B 34/30; A61B 34/32; A61B 34/37; A61B 34/74; A61B 34/76; A61B 90/06; A61B 90/361; A61B 90/37
   See application file for complete search history.

(56) References Cited

U.S. PATENT DOCUMENTS

| | | |
|---|---|---|
| 2002/0128552 A1 | 9/2002 | Nowlin et al. |
| 2003/0216715 A1 | 11/2003 | Moll et al. |
| 2007/0003061 A1 | 1/2007 | Jung et al. |
| 2009/0036902 A1 | 2/2009 | DiMaio et al. |
| 2009/0253109 A1 | 10/2009 | Anvari et al. |
| 2010/0291520 A1 | 11/2010 | Kurenov et al. |
| 2011/0137322 A1 | 6/2011 | Moll et al. |
| 2011/0144806 A1 | 6/2011 | Sandhu et al. |
| 2011/0276058 A1 | 11/2011 | Choi et al. |
| 2014/0055489 A1 | 2/2014 | Itkowitz et al. |
| 2016/0094934 A1 | 3/2016 | Yang et al. |
| 2016/0249992 A1 | 9/2016 | Ruiz Morales et al. |
| 2016/0338786 A1 | 11/2016 | Robinson et al. |
| 2017/0035521 A1 | 2/2017 | Diolaiti et al. |
| 2017/0038837 A1 | 2/2017 | Faaborg et al. |
| 2021/0401519 A1 | 12/2021 | Gomez et al. |
| 2022/0151716 A1 | 5/2022 | Gomez et al. |

OTHER PUBLICATIONS

Extended European Search Report for Application No. EP18837858.2 mailed on Jun. 3, 2020, 12 pages.
Extended European Search Report for Application No. EP18838547 mailed on Jun. 16, 2020, 14 pages.
Extended European Search Report for Application No. EP23182209.9, mailed on Oct. 9, 2023, 10 pages.
Fernandez (Ros Package Summary for Twist_mux, Nov. 13, 2014), available at http://wiki.ros.org/twist_mux , 5 Pages.
International Search Report and Written Opinion for Application No. PCT/US2018/042641, mailed on Dec. 17, 2018, 17 pages (ISRG10680/PCT1).
International Search Report and Written Opinion for Application No. PCT/US2018/042690, mailed on Dec. 17, 2018, 19 pages (ISRG10680/PCT2).
Laser Corporation: "NFC pairing video", Aug. 16, 2015, p. 1, XP054980512, Retrieved from the Internet: URL: https://www.youtube.com/watch?v=HyhgalCoB98 [retrieved on Jun. 2, 2020].
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

ASSOCIATION PROCESSES AND RELATED SYSTEMS FOR MANIPULATORS

CROSS-REFERENCE TO RELATED APPLICATIONS

This application is continuation of U.S. patent application Ser. No. 17/649,721, filed on Feb. 2, 2022, which is a continuation of U.S. patent application Ser. No. 16/633,517, filed on Jan. 23, 2020, which claims priority under 35 U.S.C. § 371 to PCT/US2018/042690 filed Jul. 18, 2018, which claims priority to both U.S. Provisional Patent Application No. 62/537,795, filed on Jul. 27, 2017 and U.S. Provisional Patent Application No. 62/551,702, filed on Aug. 29, 2017. The entire contents of each of the foregoing applications are hereby incorporated by reference.

TECHNICAL FIELD

This specification relates to association processes and related systems for manipulators, for example, for teleoperated manipulators.

BACKGROUND

Robotic manipulators can be operated to control motion of instruments in a workspace. For example, such manipulators can be used to perform non-medical and medical procedures. As a specific example, teleoperated surgical manipulators can be used to perform minimally invasive surgical procedures. An operator can control the manipulators using a user control system, e.g., connected wirelessly or via a wired connection to the teleoperated manipulators. The user control system can include multiple user input devices such that each of the teleoperated manipulators can be controlled by a distinct user input device of the user control system. The operator can thus independently control each of the teleoperated manipulators using the user input devices.

SUMMARY

In one aspect, a computer-assisted medical system includes teleoperated manipulators, a user input system, a user output system comprising a display device, and a controller configured to execute instructions to perform operations. The operations include, in a pairing mode and in response to a first set of signals generated by the user input system, causing a virtual selector shown on the display device to move relative to an imagery shown on the display device. The imagery represents a location of a first instrument supported by a first manipulator of the plurality of manipulators and a location of a second instrument supported by a second manipulator of the plurality of manipulators. The operations further include, in the pairing mode, associating the first manipulator with a portion of the user input system based on movement of the virtual selector relative to the represented location of the first instrument, and, in a following mode, controlling motion of the first instrument in accordance to a second set of signals generated by the user input system in response to operation of the portion of the user input system by a user.

In another aspect, a method of operating a computer-assisted medical system including a plurality of teleoperated manipulators is featured. The method includes causing a display device to present imagery representing a location of a first instrument supported by a first manipulator of the plurality of manipulators and a location of a second instrument supported by a second manipulator of the plurality of manipulators, and a virtual selector movable relative to the imagery in response to a first set of signals generated by a user input system. The method further includes associating, in a pairing mode, the first manipulator with a portion of the user input system based on movement of the virtual selector relative to the represented location of the first instrument, and, controlling, in a following mode, motion of the first instrument in accordance to a second set of signals generated by the user input system in response to operation of the portion of the user input system by a user.

In yet another aspect, one or more non-transitory computer readable media is featured. The one or more non-transitory computer readable media store instructions that are executable by a processing device and upon such execution cause the processing device to perform operations. The operations include causing a display device to present, imagery representing a location of a first instrument supported by a first manipulator of a plurality of teleoperated manipulators and a location of a second instrument supported by a second manipulator of the plurality of manipulators, and a virtual selector movable relative to the imagery in response to a first set of signals generated by a user input system. The operations further include associating, in a pairing mode, the first manipulator with a portion of the user input system based on movement of the virtual selector relative to the represented location of the first instrument, and, controlling, in a following mode, motion of the first instrument in accordance to a second set of signals generated by the user input system in response to operation of the portion of the user input system by a user.

Advantages of the foregoing may include, but are not limited to, those described below and herein elsewhere. For example, associations between user-operable portions of a user input system and teleoperated manipulators can be formed in a manner that is intuitive for the operator. Rather than having to interact with lists and information presented on a display that do not provide the operator with a sense of configurations or relative poses of the teleoperated manipulators, an operator can control a virtual selector overlaid on or otherwise overlapping with imagery of a workspace to initiate association between a user-operable portion and a particular teleoperated manipulator. In particular, by controlling a location of a virtual selector relative to imagery representative of a workspace of instruments supported by the manipulators, the operator can intuitively operate the user input system to associate the user-operable portion and the teleoperated manipulator.

Human-detectable feedback can be provided during the pairing mode so that the operator can be kept apprised of states and processes of devices, e.g., the user-operable portions of the user input system and the manipulators to be associated. For example, the controller can generate feedback indicative of association states of user-operable portions, the manipulators, or both the user operable portions and the manipulators. Based on the feedback, the operator can initiate association processes for devices that have not already been associated. In addition, the controller can generate feedback indicative of a proposed association prior to finalizing an association between a user-operable portion and a manipulator. This enables the operator to make adjustments to a proposed association, thereby providing the operator with greater control during the association process. In some implementations, human-detectable feedback can be continued or newly provided after an association has been made, and indicate the portion of the user input system that is associated with a particular manipulator, and vice versa. Further, the controller can disassociate a user input device or a manipulator in response to user input or a system event.

Although some of the examples described herein often refer to medical procedures and medical instruments, the techniques disclosed also apply to non-medical procedures and non-medical instruments. For example, the instruments, systems, and methods described herein may be used for non-medical purposes including industrial uses, general robotic uses, manipulation of non-tissue work pieces, and/or cosmetic improvements. Other non-surgical applications include use on tissue removed from human or animal anatomies (without return to a human or animal anatomy) or on human or animal cadavers.

The details of one or more implementations of the subject matter described in this specification are set forth in the accompanying drawings and the description below. Other potential features, aspects, and advantages will become apparent from the description, the drawings, and the claims.

BRIEF DESCRIPTION OF THE DRAWINGS

Like reference numbers and designations in the various drawings indicate like elements.

DETAILED DESCRIPTION

Example Systems

Figure 1A:
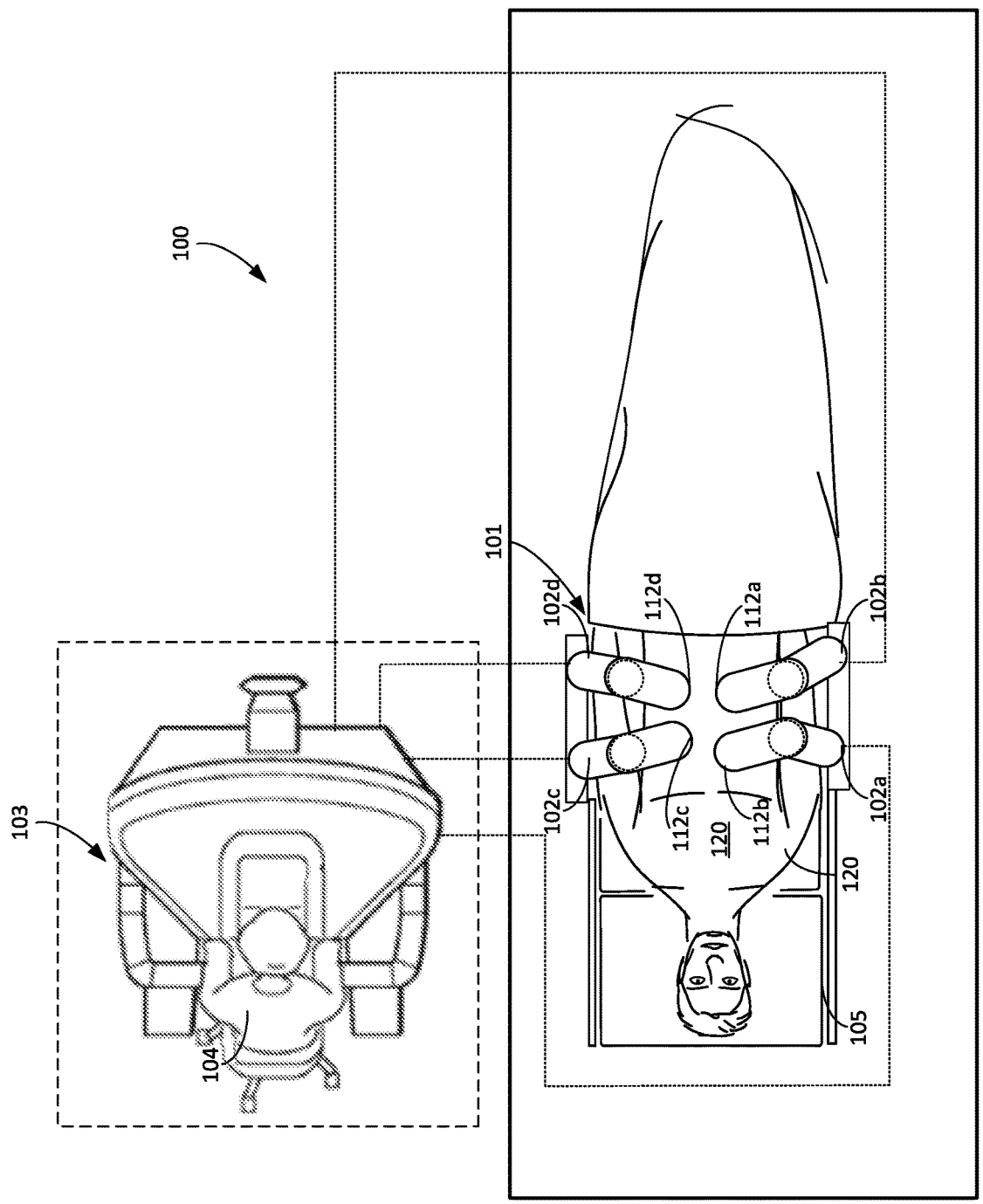
FIG. 1A is a top view of a system including a manipulator and a console.

Referring to FIG. 1A, a system 100 in an environment 10 includes a manipulator system 101 including teleoperated manipulators 102a, 102b, 102c, 102d (collectively referred to as manipulators 102 or teleoperated manipulators 102). The manipulators 102 are termed "teleoperated manipulators" because they that can be teleoperated by an operator 104 through a physically separate user input system 106. In some implementations, the manipulators 102 can also be controlled directly through manual interaction with the manipulators 102 themselves. Thus, "teleoperated manipulators" as used in this application include manipulators that can be controlled only through teleoperation, and manipulators that can be controlled through teleoperation and through direct manual control. The manipulators 102 include movable portions that can support instruments (not shown), e.g., surgical and medical instruments. The movable portions, for example, correspond to distal ends 112a, 112b, 112c, 112d of the manipulators 102.

Figure 1C:
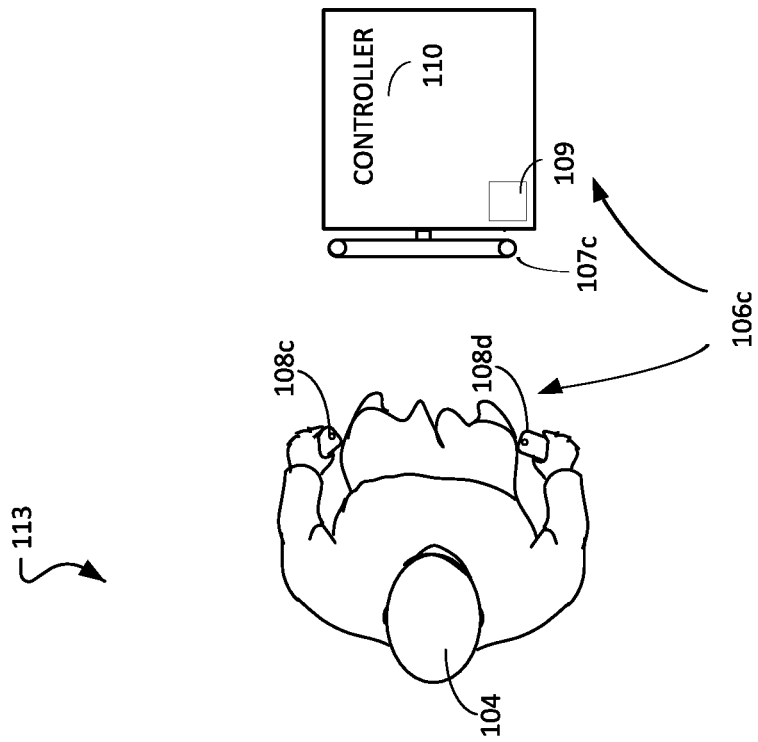
FIG. 1C is a top view of non-console based user input and user output system that can replace the console shown in 1A and 1B.
Figure 1B:
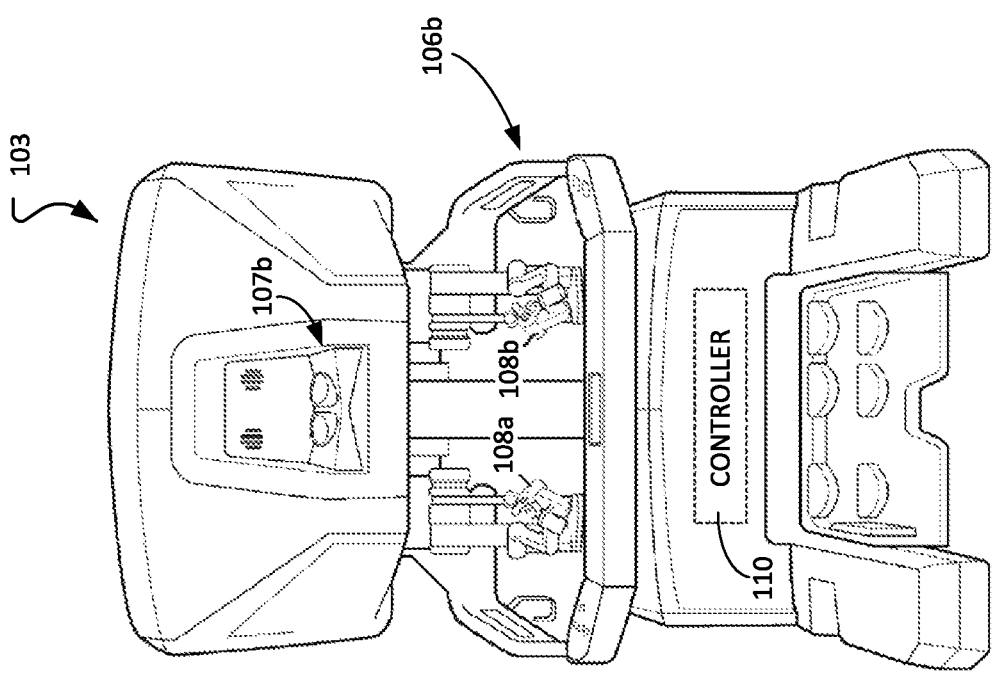
FIG. 1B is a front view of the console of FIG. 1A.

Referring also to FIGS. 1B and 1C, FIG. 1B is a front view of the console of FIG. 1A. FIG. 1C is a top view of non-console based user input and user output system that can replace the console shown in 1A and 1B. The operator 104 can teleoperate the manipulators 102 and monitor instruments supported by the manipulators 102 using a user input system and a user output system, e.g., including a display device. In some examples, such as shown in FIGS. 1A and 1B, a standalone console 103b includes the user input system 106b and the user output system. In the example shown, the console 103 includes user input system portions such as input devices 108a, 108b, and a user output system comprising a stereoscopic display device 107b).

In some examples, such as shown in FIG. 1C, a non-console based user input and output system 113 may be used. In the example shown in FIG. 1C, the user input and output system 113 includes a user input system 106c comprising handheld user input devices 108c, 108d. The handheld user input device 108c, 108d are portions of the user input system 106c whose motion is not physically constrained by links and joints to a base or console. The user input system 106c further includes a sensor system 109 that communicates with the user input devices 108c, 108d for detecting user input. The user input and output system 113 further includes a user output system including a monitor-type display device 107c that provides monoscopic or 3D images in various implementations. For convenience of explanation below, 106 is used to refer to user input systems generally and 106b, 106c are used to refer to the specific examples shown in FIGS. 1B, 1C. Similarly, 107 is used to refer to display devices comprising user output systems generally, while 107b, 107c are used to refer to the specific examples shown in FIGS. 1B, 1C.

When the system 100 is operated in a following mode, the operator 104 can operate the user input system to generate a set of user input signals to control motion of the manipulators 102. FIGS. 1B and 1C shows controller 110 as physically located with the user input and output systems. However, controller 110 may be physically separate from the user input and output systems and communicate with the user input and output systems via electronic signals transmitted via wired or wireless technology.

During operation of the system 100, the operator 104 can view the display device 107 to view imagery, e.g., two-dimensional imagery or three-dimensional imagery, representing the instruments mounted on the manipulators 102 while the manipulators 102 are being controlled by the operator 104. For example, an instrument including an image capture device such as a camera is mounted to one of the manipulators 102. The image capture device generates imagery of distal end portions of other instruments mounted to the other manipulators 102. During operation of the system 100, the operator 104 can monitor poses of distal end portions of the instruments using the imagery presented on the display device 107.

The user input system 106 is connected to the manipulators 102, e.g., wirelessly or using a wired connected. The user input system 106 includes multiple distinct portions operable by the operator 104 to control operations of the manipulators 102. These user-operable portions, in some cases, correspond to distinct user input devices. In the example depicted in FIGS. 1B and 1C, the user input system 106 includes manually operable user input devices (e.g., 108a, 108b are shown for 106b, and 108c, 108d are shown for 106c) (collectively referred to as user input devices 108) corresponding to the user-operable portions of the user input system 106 and movable relative to the manipulators 102 to control movement of the manipulators 102. The user input system 106 can include other user input devices, e.g., keyboards, touchscreens, buttons, foot pedals, etc., in addition to the user-operable portions operated to control movement of the manipulators 102 or other operations of the manipulators 102 in the following mode. These other user-operable portions can be used to allow user control of the display device 107 and otherwise allow user control of other operations of the system 100.

As described herein, in response to operation of a user-operable portion in a pairing mode, a controller 110 (shown in FIGS. 1B and 1C) of the system 100 can associate the user-operable portion of the user input system 106 with a corresponding one of the manipulators 102. When associated, the user-operable portion can be operated to control the corresponding manipulator in a following mode to perform an operation, e.g., a medical operation, a surgical operation, a diagnostic operation, etc.

Figure 2:
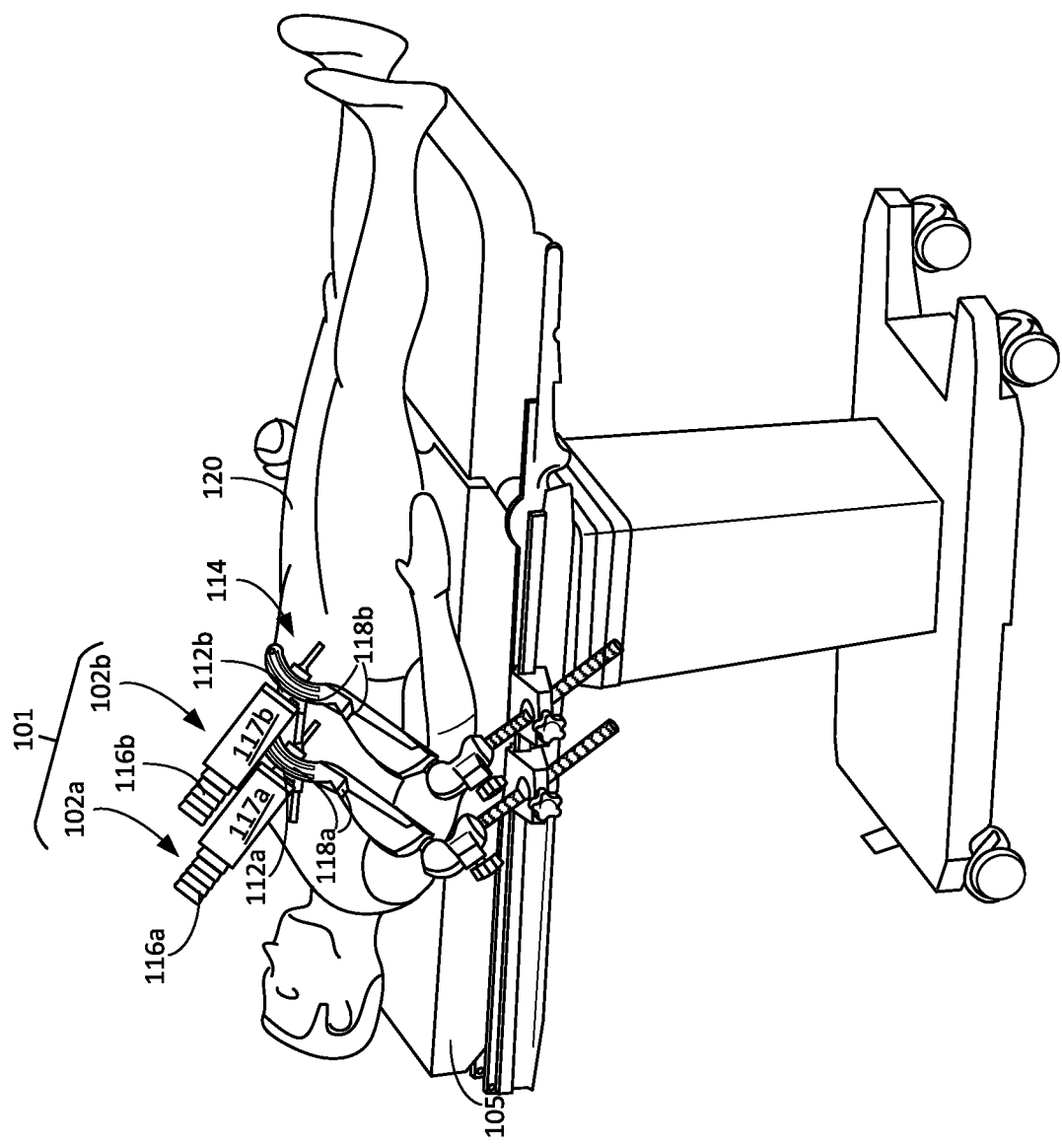
FIG. 2 is a front perspective view of a manipulator and a patient on an operating table.

FIG. 2 shows an example of the manipulator system 101. For simplicity, only the manipulators 102a, 102b of the manipulator system 101 are shown. In some implementations, the manipulator system 101 includes a single manipulators or includes three or more manipulators, e.g., four manipulators 102a, 102b, 102c, 102d as depicted in FIG. 1A.

Although FIG. 2 is described with respect to the manipulators 102a, 102b, the manipulators 102c, 102d of FIG. 1A can include features similar to those presented with respect to the manipulators 102a, 102b. The manipulators 102a, 102b, 102c, 102d may differ from one another in that different instruments may be mounted to the manipulators 102a, 102b, 102c, 102d. In addition, the manipulators 102a, 102b, 102c, 102 may be supported by an operating table 105 at different locations along the operating table 105.

The manipulators 102a, 102b include portions movable about a workspace 114. For example, these portions can correspond to distal ends 112a, 112b of the manipulators 102a, 102b that are movable about the workspace 114. The distal ends 112a, 112b support instruments 116a, 116b such that the instruments 116a, 116b can be moved about the workspace 114 when the distal ends 112a, 112b are moved about the workspace 114. In some implementations, actuation modules 117a, 117b are supportable at the distal ends 112a, 112b of the manipulators 102a, 102b. The actuation modules 117a, 117b are removably mounted to the distal ends 112a, 112b of the manipulators 102a, 102b and include one or more actuators that are operable to generate insertion and roll motions of the instruments 116a, 116b. The instruments 116a, 116b are insertable through the actuation modules 117a, 117b such that the instruments 116a, 116b are attached to the actuation modules 117a, 117b, which in turn are attached to the distal ends 112a, 112b of the manipulators 102a, 102b.

The manipulators 102a, 102b include powered joints 118a, 118b that can be driven to move the distal ends 112a, 112b of the manipulators 102a, 102b about the workspace 114. Each of the manipulators 102a, 102b includes multiple powered joints 118a, 118b that enable motion of the distal ends 112a, 112b in multiple degrees of freedom, e.g., pitch, yaw, and roll motions of the distal ends 112a, 112b of the manipulators 102a, 102b. The instruments and manipulators described herein can have one or more degrees of freedom that vary in implementations. For example, the one or more degrees of freedom include one or more of a yaw motion of the distal portion of the manipulator, a pitch motion of the distal portion of the manipulator, an insertion motion of the instrument supported by the manipulator, a roll motion of the instrument, a yaw motion of the end effector of the instrument, a wrist motion of an end effector of the instrument, or a jaw or grip motion of the end effector of the instrument.

The system 100 is a computer-assisted system. For example, the controller 110 can control operation of the system 100 and coordinate operations of the various subsystems of the system 100, including but not limited to the manipulators 102, the user input system 106, and the user output system. While schematically depicted as a controller of the console 103, in some implementations, the controller 110 can include one or more processors external to the console 103 and can be operable to control any subsystem of the system 100, e.g., the manipulators 102 and the console 103.

In some examples, the controller 110 can control operation of the actuators of the powered joints 118a, 118b as well as actuators of the actuation modules 117a, 117b. The distal ends 112a, 112b of the manipulators 102a, 102b, and hence the instruments 116a, 116b, are movable about the workspace 114 when the user-operable portions of the user input system 106 associated with the manipulators 102a, 102b are operated by the operator 104.

In a following mode, a follower of a manipulator moves in response to movement of a leader. The movement of the follower can emulate the movement of the leader. For a particular manipulator for example, the leader can be one or more of the user input devices 108, and the follower can be one or more components of the manipulator. The follower can be an end effector of the manipulator, a remote center of the manipulator, or some other component of the manipulator. In some examples, in the following mode, the distal ends 112a, 112b are the followers. For example, actuators of the powered joints 118a, 118b can be controlled to generate motion of links of the manipulators 102a, 102b about the powered joints 118a, 118b, thereby repositioning the distal ends 112a, 112b of the manipulators 102a, 102b. The motions of the distal ends 112a, 112b emulate the motions of the user input devices 108. In other examples, the motion of the user input devices 108 in the following mode can cause an instrument mounted to the distal end 112a or 112b to be ejected from the distal end 112a or 112b. In further examples, in the following mode, the actuation modules 117a, 117b can be controlled to generate insertion motion of the instruments 116a, 116b or to actuate the end effectors of the instruments 116a, 116b.

Referring to FIGS. 1A, 1B, 1C, and 2, in some implementations, the system 100 is a medical system to perform a medical procedure on a patient 120. For example, the system 100 is a diagnostic system that can be used to perform diagnostics on the patient 120. Alternatively or additionally, the system 100 is a surgical system that can be used to perform a surgical operation on the patient 120.

A variety of alternative computer-assisted teleoperated instruments 116a, 116b can be used. For example, the teleoperated instruments 116a, 116b can be surgical instruments of different types having differing end effectors. In some cases, the instruments 116a, 116b include multiple DOFs such as, but not limited to, roll, pitch, yaw, insertion depth, opening/closing of jaws, actuation of staple delivery, activation of electro-cautery, and the like. Motion in at least some of such DOFs can be generated by the actuation modules 117a, 117b of the manipulators 102a, 102b to which the instruments 116a, 116b are selectively coupled.

If the instruments 116a, 116b are medical or surgical instruments, possible end effectors include, for example, DeBakey Forceps, microforceps, and Potts scissors include first and second end effector elements that pivot relative to each other so as to define a pair of end effector jaws. Other end effectors, including scalpels and electrocautery probes, have a single end effector element. For instruments having end effector jaws, the jaws will often be actuated by squeezing the grip members of input devices. Instruments can include flexible shafts, the shafts being deflectable to enable repositioning of the distal ends of the shafts. In some cases, one or more of the instruments 116a, 116b includes an image capture device. Examples of instruments with image capture devices include endoscopes, ultrasonic probes, fluoroscopic probes, etc. The image capture device can capture imagery of other instruments in the workspace 114 (shown in FIG. 2), and this imagery can be presented to the operator 104 to allow the operator 104 to visually monitor positions of other instruments in the workspace 114. Paired user-operable portions of the user input system 106 can also be used to control actuation of the end effectors.

Figure 3A:
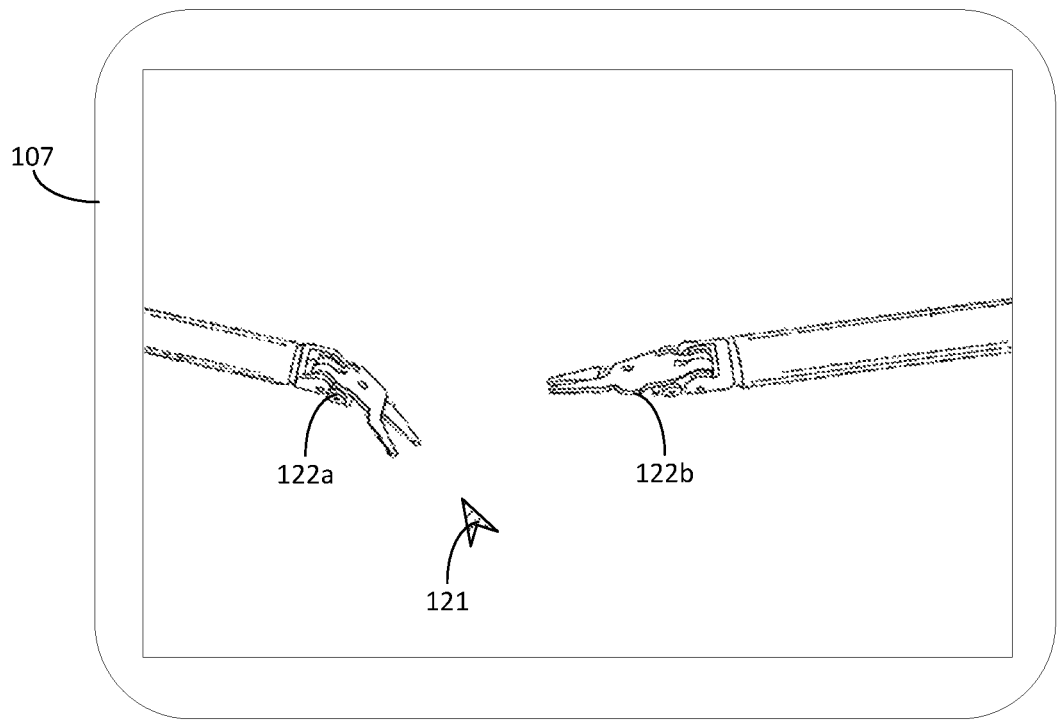
FIGS. 3A and 3B are views of a display device during a process to associate user-operable portions of a user input system with manipulators.
Figure 3B:
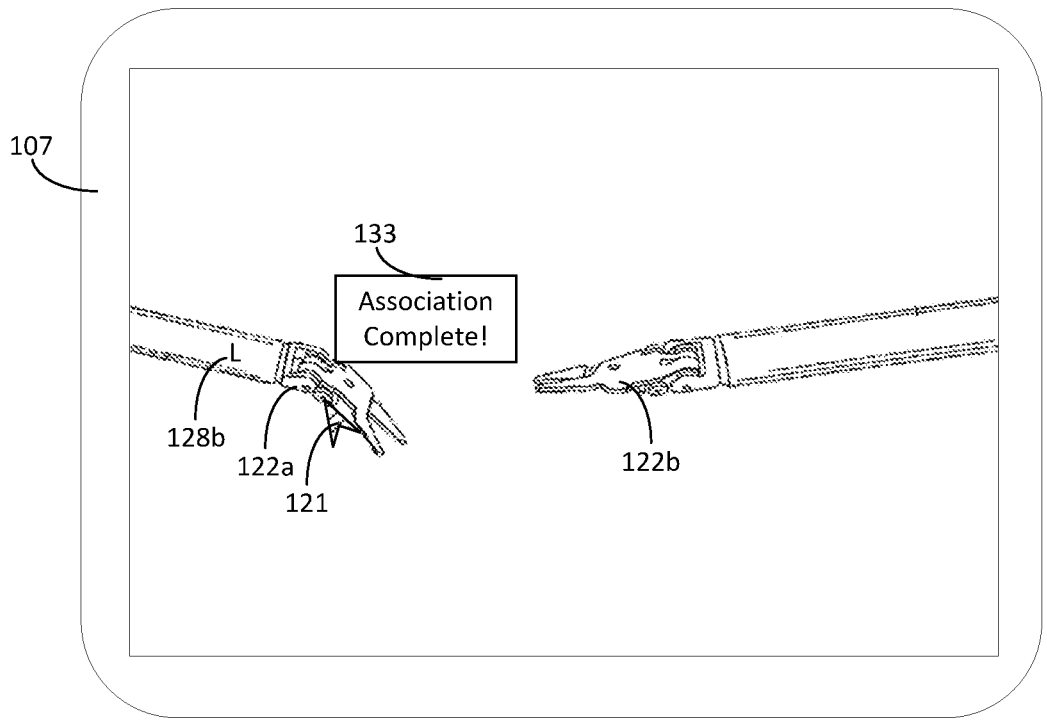
Figure 4:
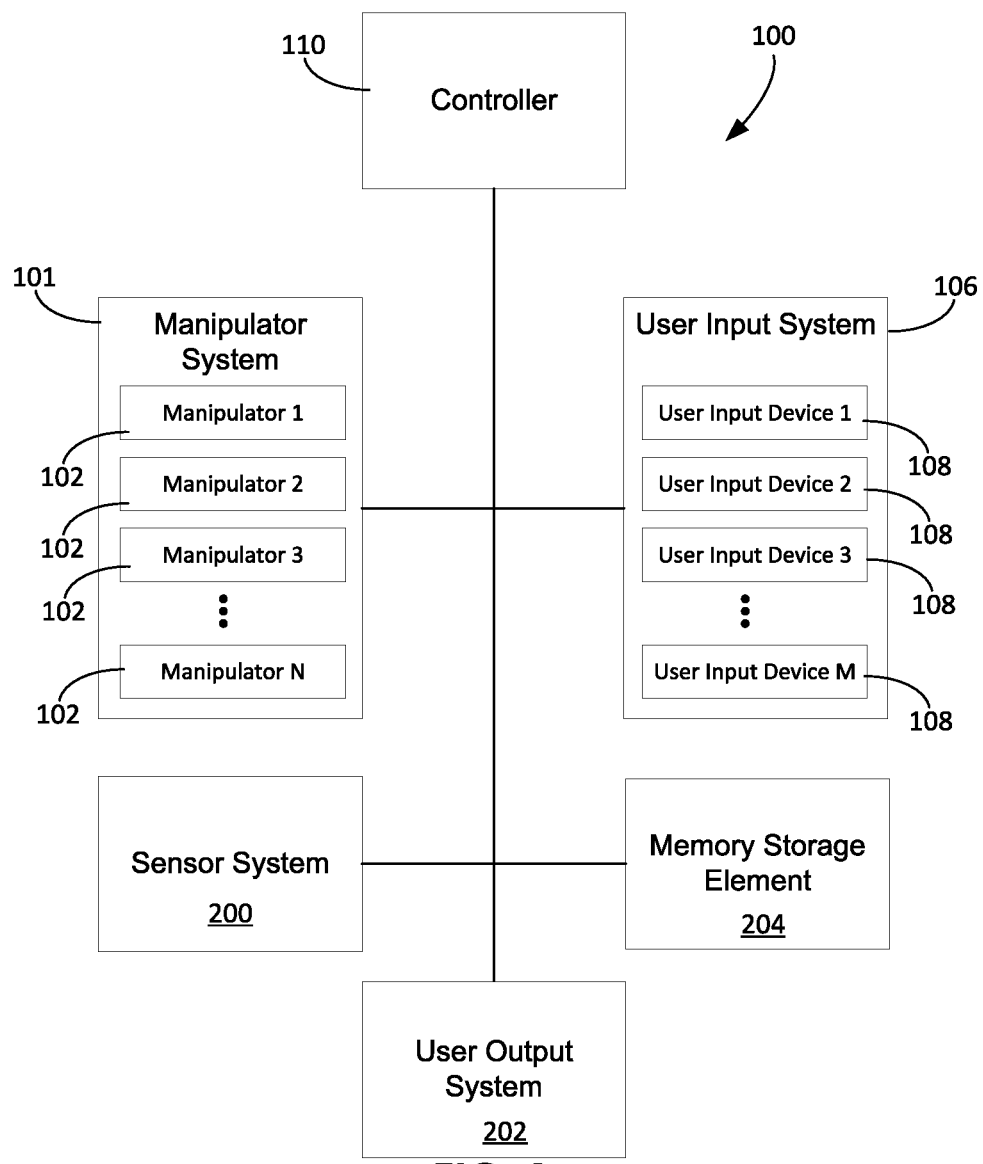
FIG. 4 is a block diagram of a system for performing a manipulator association process.

FIGS. 3A and 3B show an example of the display device 107. These examples depict the display device 107 in a pairing mode in which the display device 107 presents representations 122a, 122b of the instruments 116a, 116b and presents a virtual selector 121. In the pairing mode, the operator 104 operates the user input system 106 to reposition, e.g., to translate or to rotate, the virtual selector 121 to associate the manipulators 102a, 102b supporting the instruments 116a, 116b with corresponding user-operable portions of the user input system 106, e.g., the user input devices 108. While FIGS. 3A, 3B, and 4 are described with respect to association of the user input devices 108, in other implementations described herein, other examples of user-operable portions of a user input system can be associated with the manipulators 102a, 102b.

Turning to the example of FIGS. 3A and 3B, the imagery presented on the display device 107 is captured by one or more image capture devices. In some examples, as described herein, an image capture device is coupled to an instrument mounted to one of the manipulators 102 to capture imagery of instruments, e.g., the instruments 116a, 116b, coupled to the other manipulators 102, e.g., the manipulators 102a, 102b. In some examples, the image capture device is a stationary image capture device in the environment 10 that captures imagery of the instruments 116a, 116b.

In the example shown in FIG. 3A, the display device 107 presents imagery including the representations 122a, 122b of the instruments 116a, 116b. The representations 122a, 122b represent a location of the instrument 116a supported by the manipulator 102a and a location of the instrument 116b supported by the manipulator 102b, respectively.

The representations 122a, 122b can be part of imagery captured by an imaging system, e.g., an endoscope. The captured imagery as presented on the display device 107 is unchanged from when it is captured by the imaging system. In other examples, the representations 122a, 122b are part of imagery captured by an imaging system but then is altered in some manner. For example, the imagery can be altered to include highlighting, edge-finding, overlaid text, overlaid graphics, or other indicators. In further examples, the representations 122a, 122b are part of a synthetic image constructed in part or wholly from sensor information, e.g., collected by a sensor system 200 described herein and shown in FIG. 4. For example, the sensor information can include information collected from a shape sensing sensor or other kinematic information for joints and links of the manipulators 102a, 102b.

In implementations in which the imagery is two-dimensional imagery, a represented location of one of the instruments 116a, 116b in the imagery can be a single point in the imagery, a set of points in the imagery, or a two-dimensional region in the imagery. In implementations in which the imagery is three-dimensional imagery, a represented location of one of the instruments 116a, 116b can be a single point in the imagery, a set of points in the imagery, a two-dimensional region in the imagery, or a three-dimensional volume in the imagery. For three-dimensional imagery, two or more image capture devices or an image capture device with depth sensing or stereoscopic configuration may be used to capture imagery to form the representations shown on the display device 107.

The representations 122a, 122b of the instruments 116a, 116b in the imagery are indicative of relative poses, e.g., positions, orientations, or both, of the instruments 116a, 116b in the workspace 114 (shown in FIG. 2) of the instruments 116a, 116b. In some examples, the imagery is digital imagery captured by an image capture device coupled to another instrument in the workspace, and the representations 122a, 122b thus correspond to portions of the captured digital imagery. Alternatively or additionally, the imagery is a rendering generated based on imagery captured by the image capture device. In such cases, the representations 122a, 122b correspond to graphic indicators or portions of the rendering indicative of relative poses of the instruments 116a, 116b.

The virtual selector 121 is a graphic indicator. The virtual selector 121 has a roughly arrow-head, triangular shape in FIG. 3A; in other implementations, the virtual selector 121 may have any appropriate shape, including symmetric shapes such as circles. In some implementations, the virtual selector 121 is a two-dimensional virtual selector overlaid on two-dimensional or three-dimensional imagery presented by the display device 107. In some implementations, the virtual selector 121 is a three-dimensional virtual selector overlaid on three-dimensional imagery presented by the display device 107. In some implementations, the virtual selector 121 represents a two-dimensional or three-dimensional rigid body. In some implementations, the virtual selector 121 represents a compliant body or an assembly of components coupled with one or more joints allowing internal degrees of freedom. In some implementations, in addition to, or instead of, being defined by its geometry, the virtual selector 121 is further defined by a coloration, a pattern, a blinking light, or other graphical property. Similar to the geometry of the virtual selector, this graphical property can be symmetric or asymmetric. In other implementations, the virtual selector is an augmented reality element. For example, the virtual selector can be a graphic indicator overlaid on a portion of the environment.

A location of the virtual selector 121 (including changes in location through motion of the virtual selector 121), orientation, or a combination of location and orientation is controllable by the operator 104 through operation of the user input system 106. The virtual selector 121 has multiple degrees of freedom of motion relative to the imagery presented by the display device 107. The degrees of freedom for the virtual selector 121 allows the virtual selector 121 to be movable in the space (e.g., two-dimensional space or three-dimensional space) represented by the imagery. In some implementations, the virtual selector 121 includes fewer than six degrees of freedom, e.g., five degrees of freedom without roll in three-dimensional space, three degrees of freedom (translation and rotation) in two-dimensional space, two degrees of freedom without rotation in two-dimensional space, etc.

When the imagery and the representations 122a, 122b are three-dimensional representations, the virtual selector 121 can be translatable and rotatable in a three-dimensional space represented in the imagery. In some examples, the virtual selector 121 has six degrees of freedom, including three translational degrees of freedom (e.g., horizontal movement along a first axis, horizontal movement along a second axis, and vertical movement) and three rotational degrees of freedom (e.g., yaw, pitch, roll).

In some implementations, the imagery presented on the display device 107 can correspond to a two-dimensional projection of the workspace (including the instruments 116a, 116b), the projection being formed based on imagery captured by a two-dimensional digital imagery capture device. The imagery presented on the display device 107 represents the instruments 116a, 116b in two-dimensional space (e.g., the representations 122a, 122b are two-dimensional representations of the instruments 116a, 116b). The degrees of freedom of the virtual selector 121 can include two translational degrees of freedom and two rotational degrees of freedom.

The controller 110 is configured to, in the pairing mode, operate the display device 107 to present the virtual selector 121 for user selection of a manipulator, e.g., one of the manipulators 102, to be associated with a particular user input device. The controller 110 may operate the display device 107 in any appropriate matter. For example, the controller may directly drive the display device 107 and provide pixel-by-pixel instructions for rendering images. As another example, the controller 110 may provide one or more images for a display controller of the display device 107 to render, to blend, or to blend and render. As a further example, the controller 110 may provide directions to a coprocessor or a display processing system to determine the images to be displayed, and the coprocessor or display processing system would operate the display device 107 to display such images.

The virtual selector 121 is repositionable and/or reorientable in response to operation of the user input system 106 by the operator 104 to form an association between a particular manipulator and a particular user input device. In particular, the operator 104 controls the location and/or orientation of the virtual selector 121 relative to the representations 122a, 122b of the instruments 116a, 116b to select one of the manipulators 102 for association.

The controller 110 generates a control signal to cause the display device 107 to reposition the virtual selector 121 in response to a user input signal generated by the user input system 106 when the operator 104 operates the user input system 106. The user input signal can be generated based on an operator intent to move the virtual selector 121 in one or more degrees of freedom. In some implementations, the controller 110 receives a user input signal indicative of movement in multiple degrees of freedom and generates a control signal to cause the virtual selector 121 to move along a subset of the multiple degrees of freedom. For example, repositioning of the virtual selector 121 in one or more of the multiple degrees of freedom may not be visible to the operator 104. If the imagery is two-dimensional imagery presented on the display device 107 and the display device 107 only presents two-dimensional imagery, the subset of the multiple degrees of freedom can include a horizontal translation degree of freedom and a vertical translation degree of freedom. This subset of the multiple degrees of freedom excludes another horizontal translation degree of freedom in which motion of the virtual selector 121 would not be represented on the display device 107.

In some cases, the virtual selector 121 is axisymmetric, e.g., with respect to geometry, graphical properties, or both. For example, the virtual selector 121 is a cone, an arrow, a prism, or other axisymmetric shape. In some implementations, the virtual selector 121 is axisymmetric about one, two, or more axes. By being axisymmetric, the virtual selector 121 does not appear to be repositioned due to rotation about a particular axis. In this regard, the subset of the multiple degrees of freedom can include one or two of three available rotational degrees of freedom. This subset of the multiple degrees of freedom excludes a rotational degree of freedom about the axis about which the virtual selector 121 is axisymmetric.

FIGS. 3A and 3B illustrate a process of associating the instruments 116a, 116b or their corresponding manipulators 102a, 102b (shown in FIG. 2) to the user input devices 108 (shown in FIGS. 1B and 1C). When a pairing mode is initiated, the operator 104 operates the user input system 106 to select a user input device to be associated with a manipulator. For example, the operator 104 selects one of the user input devices 108a, 108b. After the pairing mode is initiated, referring to FIG. 3A, the display device 107 presents the virtual selector 121 at an initial location that does not satisfy an association condition to associate the user input device with a manipulator. For example, in an implementation where the proximity (e.g., graphical proximity) of the virtual selector 121 is an association condition, the initial location is not proximate to the representations 122a, 122b of the instruments 116a, 116b presented on the display device 107.

The operator 104 then operates the user input system 106 to control the location of the virtual selector 121 and reposition the virtual selector 121 relative to the imagery. This repositioning of the virtual selector 121 can be controlled by the operator 104 in a manner to select one of the representations 122a, 122b of the instruments 116a, 116b and hence select one of the manipulators 102a, 102b for association with the selected user input device. In response to operation of the user input system 106, the user input system 106 generates a set of signals for controlling a position of the virtual selector 121. In particular, the set of signals causes the display device 107 to reposition the virtual selector 121. For example, the set of signals is processed by the controller 110 to determine the virtual selector 121 should be moved relative to the imagery; then the controller 110 causes the display device 107 to reposition the virtual selector 121.

For selection of the manipulator 102a to be associated with the selected user input device, the display device 107 is controlled in a manner such that the presented virtual selector 121 is repositioned relative to the imagery to a location proximate a location of the representation 122a.

Based on the repositioning of the virtual selector 121 relative to the represented location of the instrument 116*a*, the manipulator 102*a* supporting the instrument 116*a* is associated with the user input device. The controller 110 forms an association between the manipulator 102*a* and the user input device in response to the repositioning of the virtual selector 121 relative to the represented location of the instrument 116*a* satisfying an association condition.

In some implementations, input to the user input device can reposition but cannot reorient the virtual selector 121. In other implementations, input to the user input device can reposition and reorient the virtual selector 121; the reorientation of the virtual selector 121 can be achieved using a similar technique as described for repositioning the virtual selector 121 above.

In some implementations, an association condition used in associating manipulators to user input devices does not include the orientation of the virtual selector 121. In other implementations, an association condition used in associating manipulators to user input devices includes the orientation of the virtual selector 121.

As one example of an implementation with an orientation-related association condition, the association conditions include a first condition and a second condition. The first condition corresponds to the virtual selector 121 being proximate to a location of a representation 122*a*, and the second condition corresponds to the virtual selector 121 being oriented toward the representation 122*a* (e.g. where the virtual selector 121 has an apex or a point as shown in FIG. 3A such that a longitudinal axis through the apex passes through the representation 122*a*).

Many of the following examples discussed focuses on changing the position (e.g. location) of the virtual selector 121, and the position or translational motion of the virtual selector 121 in comparison with location or motion based association conditions. However, similar to the example of FIG. 3A, the other examples discussed in this disclosure may also be implemented with association conditions that include or do not include orientation considerations.

Referring to FIG. 3B, the association condition corresponds to the virtual selector 121 overlapping with a region in the presented imagery defined the represented location of the instrument 116*a*. The user input system 106 is operated such that the virtual selector 121 is repositioned to a location proximate the represented location of the instrument 116*a* to satisfy this association condition. In some examples, referring to FIG. 3B, the region defined by the represented location of the instrument 116*a* corresponds to an area occupied by the representation 122*a* in the presented imagery. Alternatively or additionally, the region is defined by a represented location of a distal portion of the instrument 116 or a represented location of an end effector of the instrument 116*a* in the presented imagery. In an example association process, the virtual selector 121 is repositioned from its location shown in FIG. 3A to its location shown in FIG. 3B where the virtual selector 121 overlaps with an area occupied by the representation 122*a*. The overlap between the virtual selector 121 and the area corresponds to the association condition to associate the instrument 116*a* with the user input device. In this regard, when the virtual selector 121 is repositioned to achieve this overlap, the association condition is satisfied. When the association condition is satisfied, the controller 110 operates the display device 107 to present a success indicator 133.

In some implementations, the controller 110 presents visual feedback during the association process. For example, in some implementations, the controller 110 presents overlaid with or proximate to the representation 122*a* a color, number, text, graphic, or some other visual indicator to indicate association statuses or proposes associations. As specific examples, when the pairing mode is initiated, a green light or a flashing "O" near the representation 122*a* can indicate that the instrument 116*a* (and its manipulator 102*a*) is in an unassociated state, and a red light or a steadily presented (not flashing) "O" can indicate that the instrument 116*a* (and its manipulator 102*a*) is in an associated state. In some cases, a yellow light or a flashing or steadily presented "X" can provide a visual warning.

In some implementations, the controller 110 causes visual feedback indicating additional information about the statuses of the user input devices 108 with the manipulators 102. In some implementations, the visual feedback indicates which user input device is recommended to be associated with which manipulator, or indicates which user input device will be associated with which manipulator upon confirmation. As one example, where the user input device 108*a* and the instrument 116*a* (or its manipulator 102*a*) is recommended to be associated with each other, or will be associated with which manipulator upon confirmation, both the virtual selector 121 and the representation 122*a* can flash matching, similar, or identical: color, number, text, graphics, flashing sequence, or other visual feedback.

In some implementations, the controller causes visual feedback indicating which user input device has been, or is currently, associated with which instrument or manipulator. As one example, after the user input device 108*a* is associated with the instrument 116*a* (or its manipulator 102*a*) the controller 110 can steadily present a color, number, text, graphical pattern, or other visual feedback indicative of the association near the appropriate representation of the instrument. In various implementations, this steady presentation of color, number, text, graphics, or other textual feedback can last for the entire duration during which that user input device is associated with that instrument.

In the example shown in FIG. 3B, the controller 110 has caused an association indicator 128*b* (shown as a letter "L") to appear overlaid with the representation 122*a* to indicate the instrument 116*a*'s association status with an input device identified by "L". The association indicator 128*b* can be presented for part or the entire duration during which the user input device 108*a* is associated with the instrument 116*a*.

Other examples of association conditions are described with respect to FIGS. 7A-7E.

Referring to FIG. 4 and as described herein, an example of the system 100 for performing an association process includes the manipulator system 101, the controller 110, a user output system 202, and the user input system 106. While described with respect to FIGS. 1, 2, 3A, and 3B as including four manipulators, in some implementations, as shown in FIG. 4, the manipulator system 101 can include any number of manipulators. For example, the manipulator system 101 includes N manipulators (e.g., Manipulator 1 through Manipulator N, collectively referred to as manipulators 102). Similarly, while described with respect to FIGS. 1, 2, 3A, and 3B as including two user input devices, in some implementations, as shown in FIG. 4, the user input system 106 includes any number of user input devices or user-operable portions of the user input system 106. For example, the user input system 106 includes M user input devices (e.g., User Input Device 1 through User Input Device M, collectively referred to as user input devices 108). Examples of the user input devices 108 include: joysticks, touchscreens, gloves, foot pedals, touchscreens, or handheld remotes.

In some implementations, the system 100 includes a sensor system 200. The sensor system 200 includes sensors operable to detect movement of the user input devices 108. The sensor system 200 can detect poses, e.g., positions, orientations, or both positions and orientations, of the user input devices 108 and the manipulators 102 in the environment 10. Sensors of the sensor system 200 include, for example, infrared sensors, ultrasonic sensors, image capture devices, accelerometers, position encoders, optical sensors, or other appropriate sensors for detecting motion and poses of the manipulators 102 and the user input devices 108.

The user output system 202 provides human-perceptible feedback to the operator 104 and includes the display device 107. The feedback provided by the user output system 202 can include feedback provided during an association process or during the following mode to provide guidance to the operator 104 for controlling the virtual selector 121 or for controlling the manipulators 102, respectively. Furthermore, the user output system 202 is operable to present the virtual selector 121 (e.g., on the display device 107) during the pairing mode to enable the operator 104 to select a user input device and a manipulator for associating with one another. In some implementations, the user output system 202 and the user input system 106 correspond to the console 103.

Figure 5:
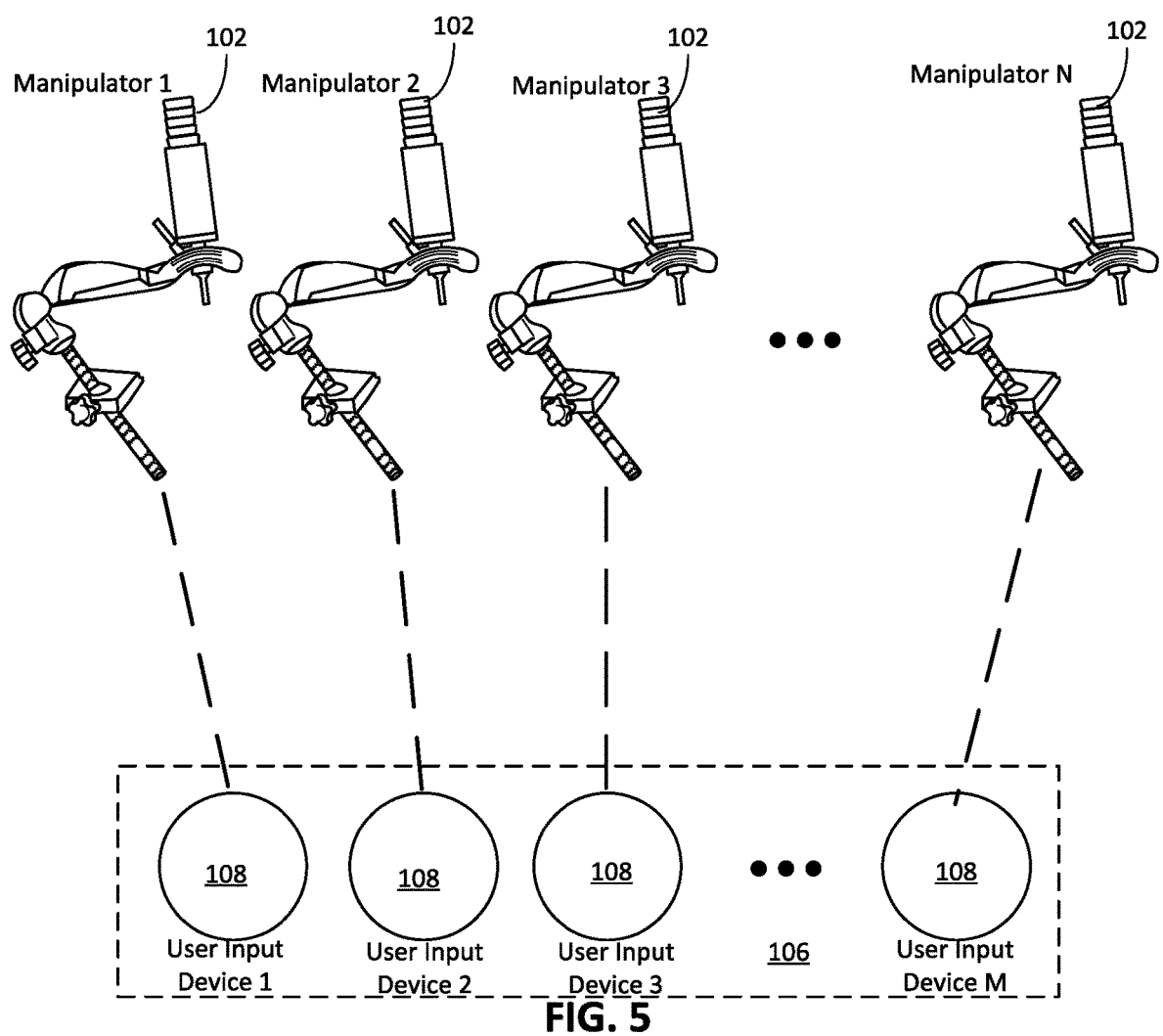
FIG. 5 illustrates associations between manipulators and user-operable portions of a user input system.

The system 100 can further include a memory storage element 204. The memory storage element 204 can store data indicative of associations formed between the manipulators 102 and the user input devices 108. The controller 110 can retrieve these stored data to determine whether a user input device or a manipulator is in an associated state or an unassociated state. Referring to FIG. 5, the manipulators 102 and the user input devices 108 are associated so that each user input device 108 is associated with a distinct manipulator 102. As a result, the user input devices 108 can be controlled by the operator 104 so that the associated manipulators can be independently controlled. In some cases, each of the manipulators 102 is associated with a corresponding one of the user input devices 108. As a result, each of the manipulators 102 can be controlled using the user input devices 108.

Example Processes

Figure 6:
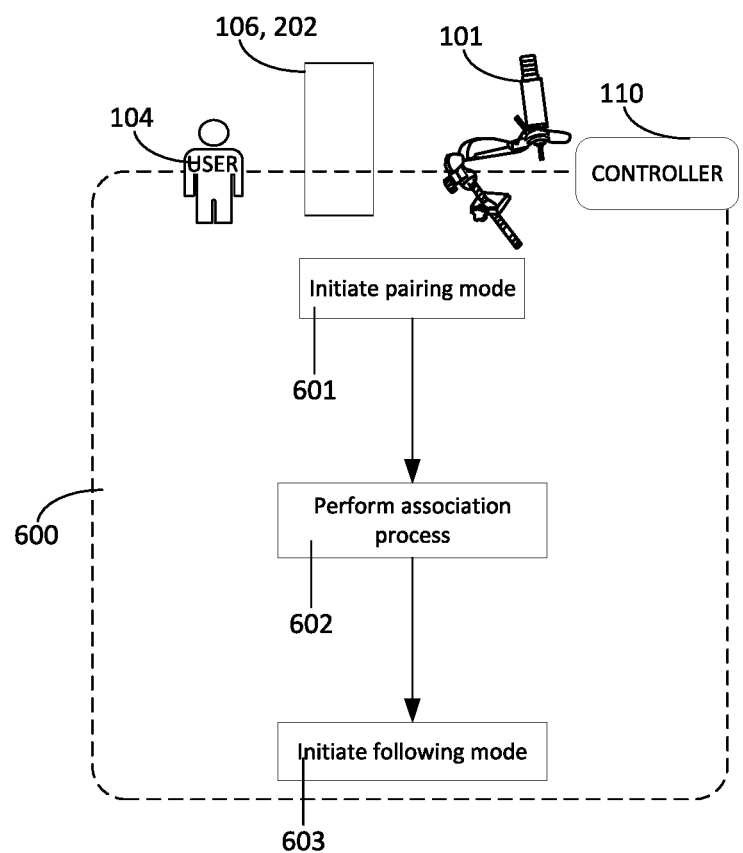
FIG. 6 is a flowchart illustrating a process of operating a user input system to control a manipulator.

Referring to FIG. 6, a process 600 including an association process and a following process is presented with respect to the system 100 described herein. The process 600 is performed by the user input system 106 and the user output system 202, the manipulator system 101, the controller 110, other portions of the system 100 (e.g., the console 103, the system 113), or a combination of the foregoing. At operation 601, a pairing mode is initiated to associate one or more user-operable portions of the user input system 106 with one or more manipulators of the manipulator system 101. At operation 602, the association process is performed to associate a particular manipulator with a particular user-operable portion of the user input system 106. The particular manipulator and the particular user-operable portion can both be selected by the operator 104. Examples of further operations and sub-operations the operations 601 and 602 are described with respect to FIGS. 7A-7E, 8A, 8B, and 9.

At operation 603, a following mode is initiated so that, in a following process, the manipulator can be controlled in response to operation of the user-operable portion. In some implementations, in the following mode, the manipulator associated with the user-operable portion at operation 602 can be moved in response to operation of the user-operable portion by the operator 104. In response to operation of the user-operable portion, the user input system 106 generates a set of user input signals for controlling a position of the manipulator. The controller 110 then generates a corresponding set of control signals based on the set of user input signals. The set of control signals are transmitted to the manipulator to move the manipulator with which the user-operable portion is associated (e.g., during the pairing mode). This causes the manipulator and an instrument mounted to the manipulator to move. In this regard, the user-operable portion and the manipulator form a leader-follower system in which the user-operable portion is a leader device and the manipulator is a follower device, thereby enabling the manipulator to be teleoperated through operation of the user-operable portion. If the system 100 is a surgical system, an instrument supported by the manipulator can be controlled to perform a surgical operation on a patient.

Figure 7A:
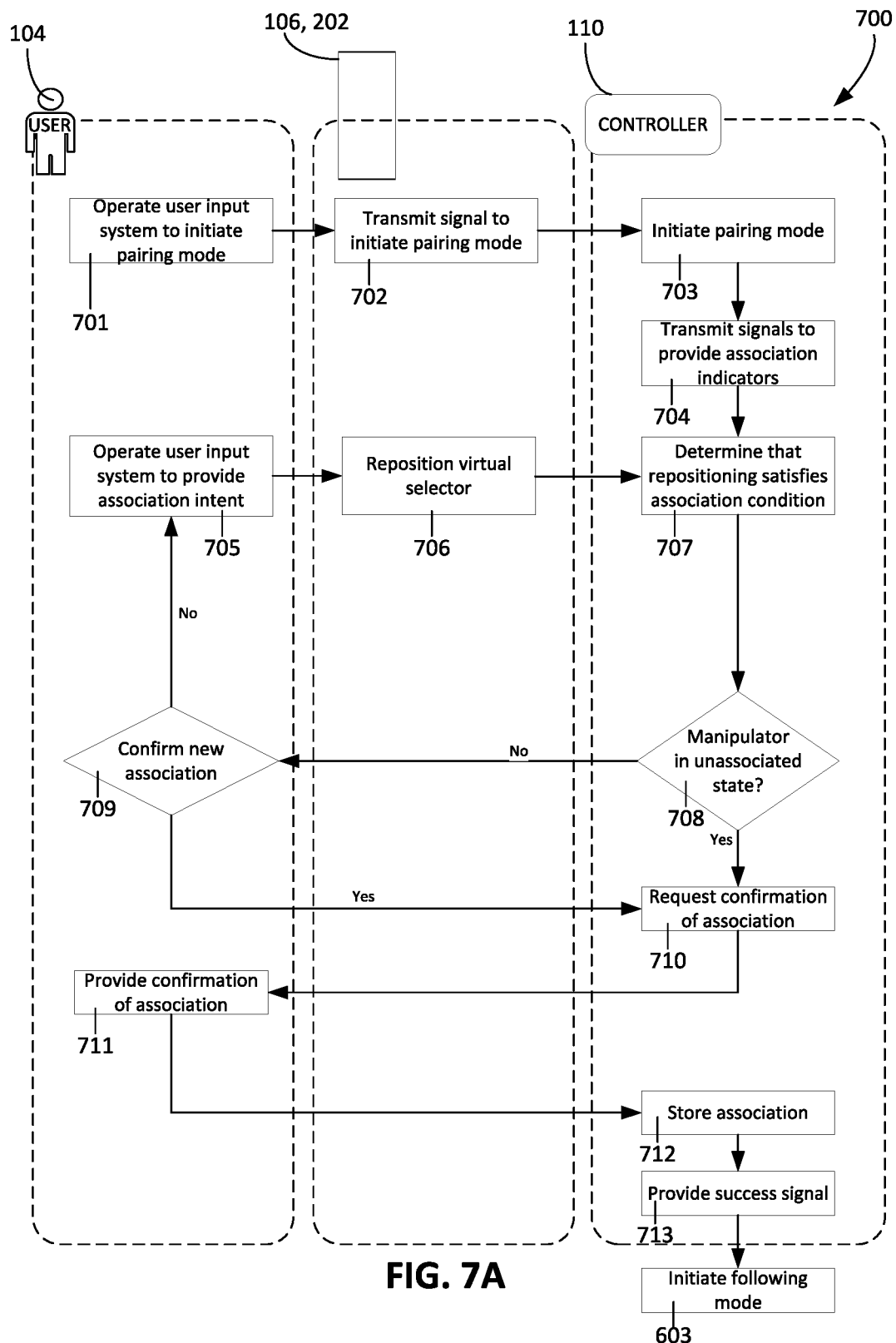
FIG. 7A is a flowchart illustrating a process to associate a user-operable portion with a manipulator.

FIG. 7A illustrates an example of an association process 700 to associate a particular user-operable portion of the user input system 106 with a particular manipulator of the manipulator system 101. The process 700 is performed, for example, during the operations 601 and 602 described with respect to the process 600.

Operations 701-703 of FIG. 7A illustrate an example set operations for initiating a pairing mode. At operation 701 of the process 700, the operator 104 operates the user input system 106 to initiate the pairing mode. For example, the user input system 106 includes a user-operable portion dedicated to initialization of the pairing mode, and the operator 104 operates the dedicated user-operable portion to initialize the pairing mode. This dedicated user-operable portion can correspond to a button that initiates the pairing mode when manually operated by the operator 104. At operation 702, the user input system 106 transmits a signal to the controller 110 to initiate the pairing mode. At operation 703, the controller 110 initiates the pairing mode.

Once in the pairing mode, a particular user-operable portion is selected for association. For example, the operator 104 operates the user input system 106 to select a user-operable portion. Alternatively, the controller 110 automatically selects one of the user-operable portions for association. In the pairing mode, the operator 104 further provides an association intent to associate the particular user-operable portion with a particular manipulator. In addition, feedback is provided to the operator 104 so that the operator 104 can be kept informed of states of the manipulators of the manipulator system 101 and the user-operable portions of the user input system 106. Operations 704-713 illustrate examples of operations that occur during the pairing mode.

In some implementations, after the pairing mode is initiated at operation 703, at operation 704, the controller 110 transmits signals to provide association indicators to the operator 104. The signals can be transmitted to the user output system 202. The user output system 202 presents the association indicators to indicate association states of each of the manipulators of the manipulator system 101.

Figure 7B:
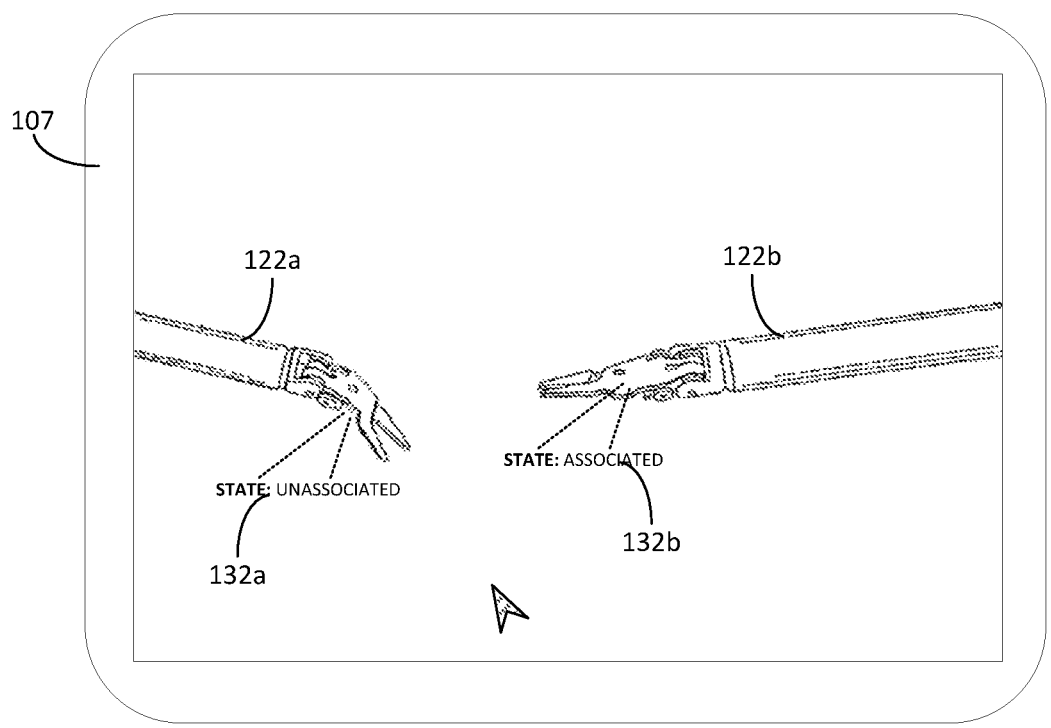
FIGS. 7B-7E are views of a display device during a process to associate user-operable portions of a user input system with manipulators.

FIG. 7B illustrates an example of visual feedback that can be provided at the operation 703. The visual feedback includes association indicators to provide information indicative of association states of the manipulators 102a, 102b (not shown). The association states of the manipulators 102a, 102b can be unassociated or associated, with an unassociated state indicating that a manipulator has not been associated with a user-operable portion and an associated state indicating that a manipulator has already been associated with a user-operable portion.

Referring to FIG. 7B, the display device 107 can present visual feedback including a state indicator 132a for the manipulator 102a supporting the instrument 116a and a state indicator 132b for the manipulator 102b supporting the instrument 116b. The state indicators 132a, 132b are positioned proximate distal portions of the representations 122a, 122b of the instruments 116a, 116b. The state indicator 132a indicates that the manipulator 102a is in an unassociated state, while the state indicator 132b indicates that the manipulator 102b is in an associated state. The state indicators 132a, 132b can visually inform the operator 104 of the association states of the manipulators 102a, 102b so that the operator 104 can provide association intent in view of the association states of the manipulators 102a, 102b.

Turning back to FIG. 7A, at operation 705, the operator 104 operates the user input system 106 to provide an association intent. For example, the user input system 106 generates the set of user input signals for controlling the position (e.g., location) and/or orientation of the virtual selector 121. The set of user input signals is generated in response to the operation of the user input system 106. The following discussion focuses on controlling the position of the virtual selector 121. In implementations where the orientation of the virtual selector 121 is also controlled, a similar process may be used to orient and reorient the virtual selector 121.

In some implementations, the operator 104 operates a user-operable portion of the user input system 106 to generate the set of signals. The user-operable portion that is operated can correspond to the particular user-operable portion to be paired with a manipulator. In other implementations, the user input system 106 includes a user-operable portion dedicated for use by the operator 104 to cause repositioning of the virtual selector 121. In this regard, the user-operable portion operated to control the position and the orientation of the virtual selector 121 can be different from the user-operable portions that can be associated to the manipulators.

At operation 706, in response to the set of user input signals generated by the user input system 106, the user output system 202 of the console 103 repositions the virtual selector 121 (described with respect to FIGS. 3A and 3B) relative to the imagery presented by the user output system 202. For example, the controller 110 generates the set of control signals in response to the set of user input signals and transmits the set of control signals to the user output system 202 to control the position and orientation of the virtual selector 121.

The repositioning of the virtual selector 121 can occur in a number of manners. In some implementations, the virtual selector 121 is movable relative to the imagery in response to the set of signals generated by the user input system 106. The virtual selector 121 moves along a continuous path from a first position to a second position in response to the set of signals. For example, the user-operable portion includes a user input device such as a joystick, and the virtual selector 121 moves relative to the imagery in response to manual manipulation of the joystick. The user output system 202 presents the virtual selector 121 on the display device 107 such that, when viewed by the operator 104, the virtual selector 121 appears to translate across the display device 107. Similarly, the virtual selector 121 is movable through orientations between a first orientation and a second orientation in response to the set of signals. In this regard, the virtual selector 121 appears to rotate continuously.

In some implementations, rather than being moved across the display device 107 relative to the imagery, the virtual selector 121 is repositioned on the display device 107 from a first position to a second position on the display device 107 without moving along a path from the first position to the second position. Alternatively or additionally, the virtual selector 121 is repositioned on the display device 107 from a first orientation to a second orientation without continuously rotation from the first orientation to the second orientation. The user input system 106 is operated to select a location or an orientation of the virtual selector 121 after repositioning, e.g., the second position or the second orientation of the virtual selector 121. For example, the user input system 106 can include a touchscreen, and the operator 104 selects the location by touching a portion of the touchscreen. In response to this selection, the display device 107 presents the virtual selector 121 at the second position or the second orientation absent any movement of the virtual selector 121 between the first position and the second position or between the first orientation and the second orientation.

Turning back to FIG. 7A, at operation 707, the controller 110 determines whether the repositioning of the virtual selector 121 satisfies an association condition. Association conditions can vary between implementations. Association conditions can include a condition for a position of the virtual selector 121, a condition for an orientation of the virtual selector 121, or an amount of time that the virtual selector 121 is at a particular position or within a region. Also, as discussed in connection with FIG. 3A and applicable to the various examples disclosed herein, association conditions can include a condition based on an orientation of the virtual selector 121.

Figure 7C:
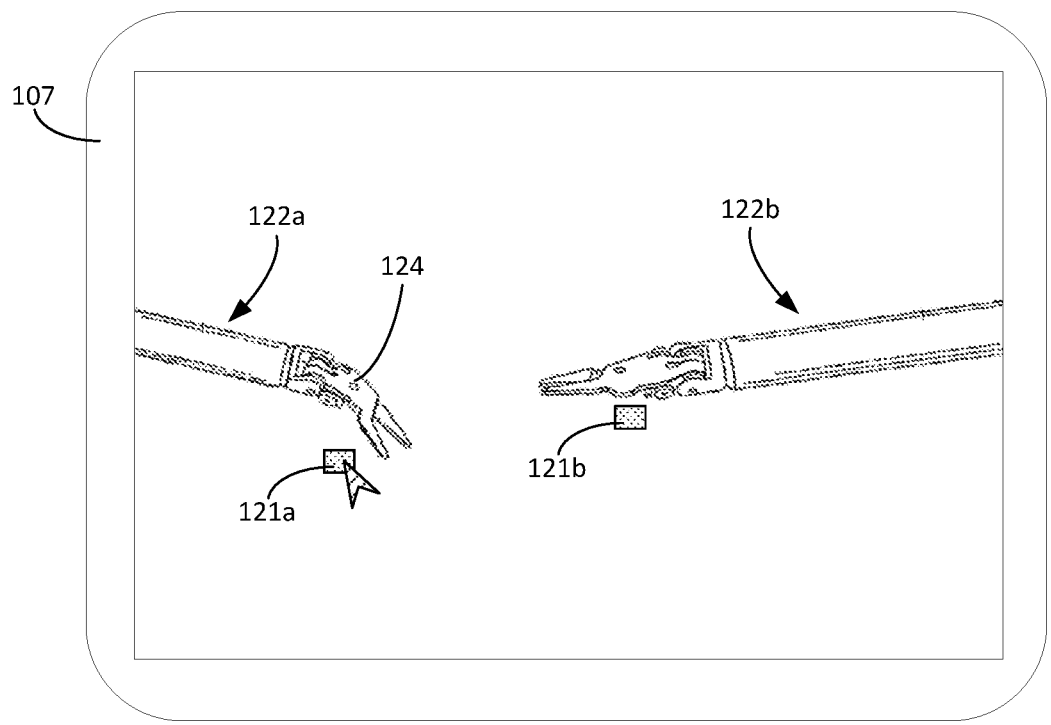

In some implementations, referring to FIG. 7C, the association condition to associate the instrument 116a with the user-operable portion corresponds to the virtual selector 121 being repositioned to a location on or proximate the representation 122a of the instrument 116a. In some cases, the display device 107 presents selectable indicators 121a, 121b proximate the representations 122a, 122b. In some cases, the selectable indicators 121a, 121b do not overlap with the representations 122a, 122b. The association condition is satisfied when the virtual selector 121 is repositioned on or proximate one of the selectable indicators 121a, 121b. For example, the virtual selector 121 overlaps the selectable indicator 121a to satisfy the association condition for associating the user-operable portion with the manipulator 102a, or the virtual selector 121 overlaps the selectable indicator 121b to satisfy the association condition for the associating the user-operable portion with the manipulator 102b.

Figure 7D:
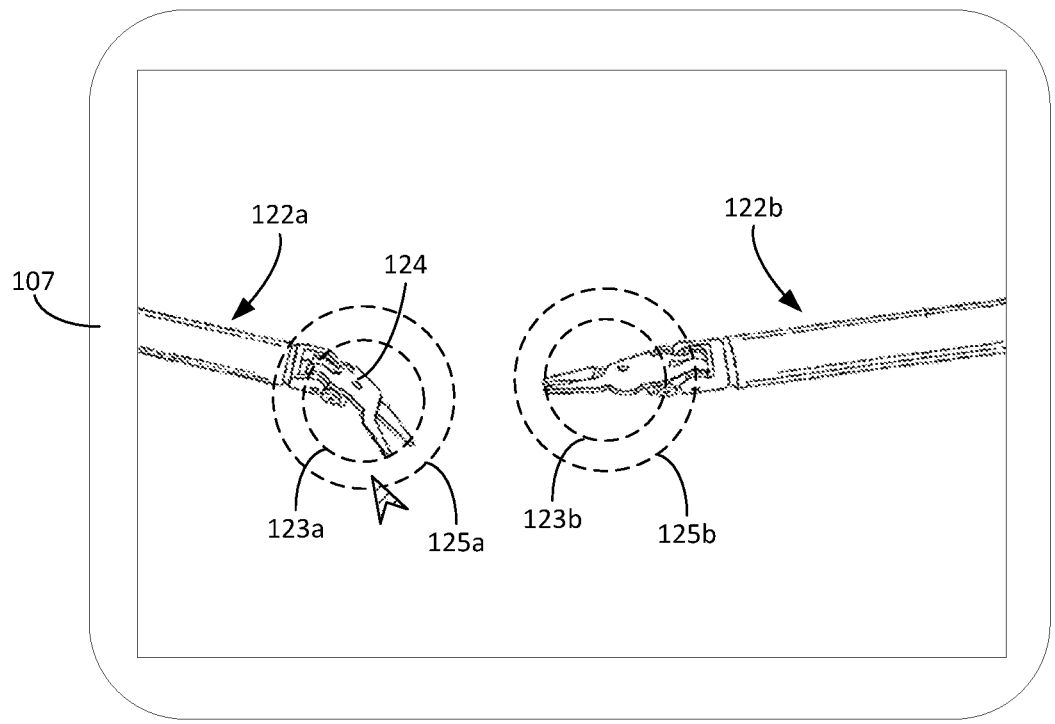

In some implementations, referring to FIG. 7D, the association condition to associate the manipulator 102a with the user-operable portion corresponds to the virtual selector 121 being positioned within a region 123a surrounding the representation 122a. For example, the region 123a includes a combination of (i) an area in the imagery covered by a portion 124 of the representation 122a representing the end effector of the instrument 116a and (ii) an area in the imagery surrounding the portion 124. The virtual selector 121 can thereby trigger association with the manipulator 102a without overlapping with the area in the imagery covered by the representation 122a.

In some implementations, the region 123a is defined by a predefined distance to a particular point on the representation 122a. The particular point can be, for example, a centroid of the area covered by the representation 122a, a centroid of the area covered by the portion 124 of the representation 122a, or another point along the representation 122a. Alternatively or additionally, the region 123a is a shape that has a predefined size and that bounds the representation 122a or bounds the portion 124 of the representation 122a. The shape of the region 123a can be, for example, rectangular, circular, ovular, or another appropriate shape.

The association condition can be satisfied immediately when the virtual selector 121 is repositioned into the region 123a. In some implementations, the controller 110 further requires that the virtual selector 121 is positioned within the region 123a for a predefined period of time, e.g., 0.5 seconds to 2 seconds, before the association condition is considered satisfied. In some implementations, the controller 110 further requires that the virtual selector 121 be substantially stationary within the region 123a for the predefined period of time.

In some implementations, as the virtual selector 121 is being repositioned during the pairing mode, the controller 110 provides feedback to the operator 104. The controller 110 provides the feedback in response to repositioning of the virtual selector 121. For example, referring to FIG. 7D, the virtual selector 121 is repositioned into a region 125a proximate the representation 122a. For example, the region 125a surrounds the representation 122a as well as the region 123a. The region 125a thus encompasses at least the portion 124 of the representation 122a.

In some implementations, the repositioning of the virtual selector 121 that satisfies the association condition corresponds to movement of the virtual selector 121 toward the representation 122a of the instrument 116a. For example, the association condition is satisfied when a velocity or an acceleration of the virtual selector 121 is defined by a vector that intersects the represented location of the instrument 116a or the region 123a.

Figure 7E:
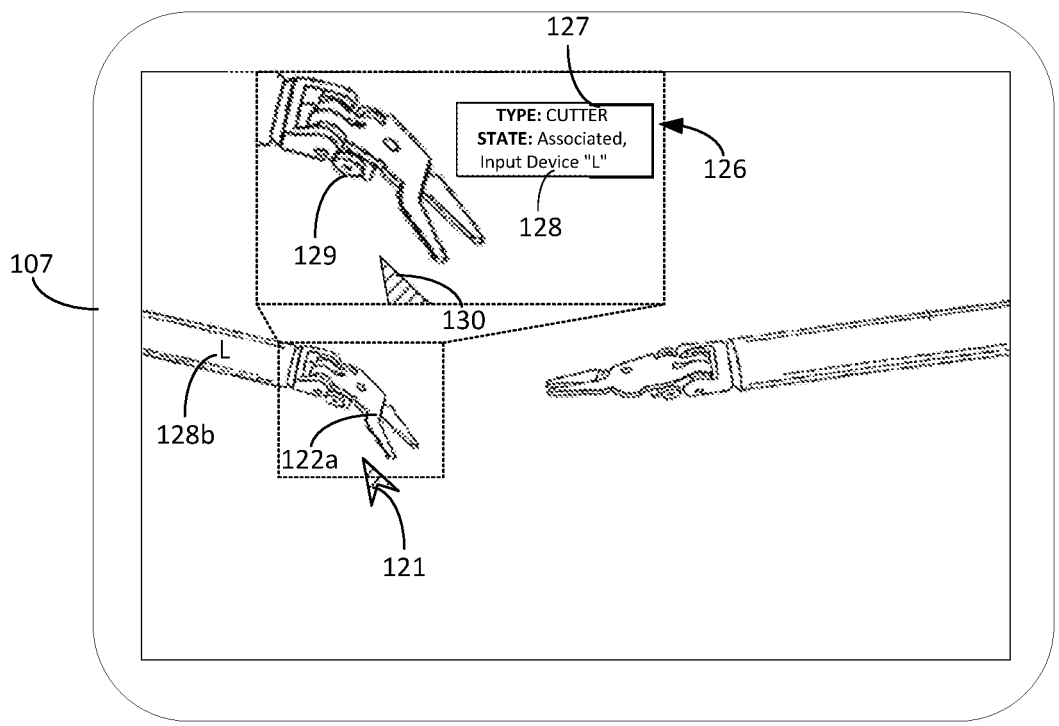

FIG. 7E illustrates an example of visual feedback provided to the operator 104 through the display device 107 after the virtual selector 121 is repositioned to be within the region 125a. In response to the virtual selector 121 being repositioned into the region 125a, the display device 107 presents an information box 126, e.g., a tooltip, including information pertaining to the instrument 116a and the manipulator 102a, including a type 127 of the instrument 116a and an association state 128 of the manipulator 102a. The association state 128 may include any appropriate amount of information regarding association status. In some implementations, the association state 128 indicates just "associated" or "unassociated." In some implementations, the association state 128 indicates with which input device the instrument 116a is associated. In the example shown in FIG. 7E, the association state 128 states that the state is "Associated" with Input Device 'L'", and is supplemented with an association indicator 128b ("L") overlaid or proximate the representation 122a.

The association state 128 and association indicator 128b can be indicated by any one or combination of color, number, text, graphical pattern, or other visual feedback. In some embodiments where the input device 108 include visual feedback devices such as lights or displays, the input devices can also present matching, similar, or identical colors, numbers, text, graphics, or other visual feedback as the ones used for the representation of the associated instrument. In various implementations, the association indicator 128b is presented for part or the entire duration during which the user input device 108a is associated with the instrument 116a.

As shown in the example of FIG. 7E, the instrument 116a is a cutter, and the association state of the manipulator 102a is an unassociated state. The display device 107 is also operated to provide an enlarged representation 129 of the instrument 116a as the virtual selector 121 approaches the representation 122a. The enlarged representation 129 can provide visual confirmation to the operator 104 that the instrument 116a is the desired instrument for association with the user-operable portion. The operator 104 may be able to more easily identify the instrument 116a through the enlarged representation 129.

An enlarged representation 130 of the virtual selector 121 can also be presented so that the operator 104 can monitor movement of the virtual selector 121 relative to the representation 122a by monitoring movement of the enlarged representation 130 relative to the enlarged representation 129. These enlarged representations 129, 130 can allow selection of the instrument 116a to be easier by providing the operator 104 with a larger target for selection using the virtual selector 121.

Turning back to FIG. 7D, in some implementations, the virtual selector 121 is repositionable into a region 123b for association with the instrument 116b. The region 123b can have features similar to features of the region 123a. Similarly, while repositioning of the virtual selector 121 into the region 125a for the instrument 116a is described for triggering feedback to be provided to the operator 104, in some implementations, the virtual selector 121 is repositioned into a region 125b for triggering feedback to be provided. Movement of the virtual selector 121 can trigger provision of feedback related to the instrument 116b.

In some implementations, the controller 110 associates the manipulator with the user-operable portion only if the user-operable portion of the user input system is in an unassociated state. Turning back to FIG. 7A, after the controller 110 determines that repositioning of the virtual selector 121 satisfies the association condition for a particular manipulator, at operation 708, the controller 110 determines an association state of the manipulator. The controller 110 determines whether the manipulator is in an unassociated state. For example, the controller 110 can access the memory storage element 204 (shown in FIG. 4) to determine whether an association for the manipulator has been stored on the memory storage element 204. If the manipulator is not in an unassociated state, e.g., is in an associated state, the operator 104 at operation 709 either confirms that a new association is to be provided to the manipulator or indicates that the manipulator should maintain the stored association. If the operator 104 indicates that the manipulator should maintain the stored association, the operator 104 operates the user input system at the operation 705 to provide another association intent to select another one of the manipulators.

If the operator 104 confirms that a new association is to be provided, the controller 110 can remove the stored association for the manipulator. If it is confirmed at the operation 709 that a new association is to be created for the manipulator or if it is determined at the operation 708 that the manipulator is in an unassociated state, the controller 110 at operation 710 requests for user confirmation of an association between the user-operable portion and the manipulator. For example, the controller 110 transmits data representing the request for confirmation to the user output system 202.

At operation 711, the operator 104 provides the confirmation of the association. In some implementations, the operator 104 can provide this confirmation by operating the user input system 106. For example, the operator 104 can cause the virtual selector 121 to move to a predefined region presented on the display device 107 to confirm the association. The predefined region can correspond to a selectable button presented on the display device 107.

At operation 712, after receiving confirmation of the association, the controller 110 stores the association, e.g., in the memory storage element 204. The controller 110 then provides a success signal at operation 713. For example, the user output system 202 is operated to provide a human-perceptible signal indicative of the success of the association between the manipulator and the user input element. The human-perceptible success signal can correspond to the success indicator 133 described with respect to FIG. 3B.

While described with respect to associating a single user-operable portion with a single manipulator, in some implementations, operations 704-713 can be repeated to associate other user-operable portions of the user input system 106 with other manipulators of the manipulator system 101. The system 100 can remain in the pairing mode until the operator 104 operates the user input system 106 to provide input indicative of initiating the following mode, e.g., initiating operation 603. In the following mode, the user-operable portions that have been associated with the manipulators can be operated by the operator 104 to control movement of the manipulators.

Figure 8A:
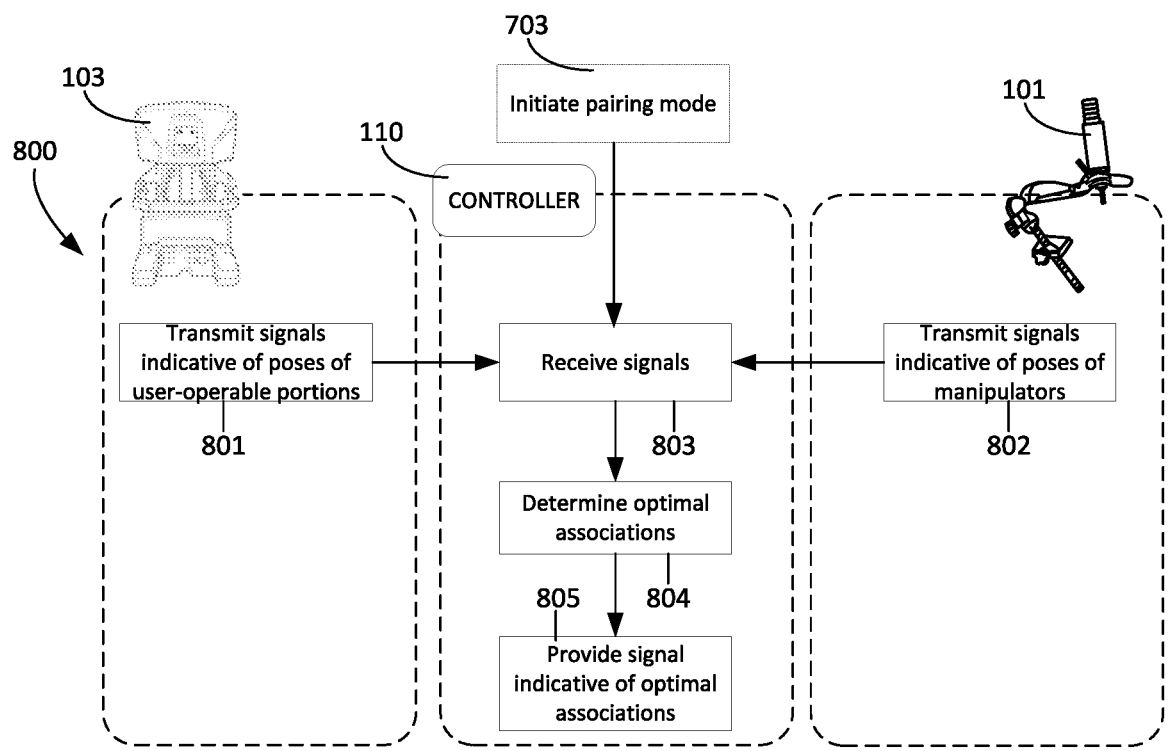
FIG. 8A is a flowchart illustrating a process to optimize associations formed between manipulators and user-operable portions of a user input system.

In some implementations, the controller 110 can provide recommendations to optimize the associations formed between the manipulators and the user-operable portions. Process 800 of FIG. 8A illustrates an example process to provide such a recommendation. The process 800 is initiated after the pairing mode is initiated. Upon initiation of the pairing mode, at operation 801, the user input system 106 transmits signals indicative of poses of the user-operable portions of the user input system 106, e.g., poses of the user-operable portions in the environment 10 (shown in FIG. 1A). At operation 802, the manipulator system 101 transmits signals indicative of poses of the manipulators of the manipulator system 101 to the controller 110. At operation 803, the controller 110 receives these signals from the user input system 106 and the manipulator system 101. In some implementations, the sensor system 200 detects the poses of the user-operable portions, the manipulators, or both and transmits these signals to the controller 110. In addition, the controller 110 further receives a signal indicative of the position and the orientation of the image capture device, e.g., on the instrument supported on the manipulator 102c.

The controller 110 receives the signals and uses kinematic modeling to determine the positions and orientations of the manipulators 102a, 102b, the positions and orientations of the instruments 116a, 116b, and the position and orientation of the image capture device. In some cases, one or more signals are generated by sensors of the manipulators (e.g., the manipulators 102a, 102b, and the manipulator to which the image capture device is mounted) or sensors of the instruments (e.g., the instruments 116a, 116b, and the image capture device). The sensors of the manipulators include, for example, accelerometers, gyroscopes, encoders, or other sensors associated with joints of the manipulators 102a, 102b. The sensors of the instruments include, for example, shape sensors through shafts of the instruments. Alternatively, the positions and orientations of the manipulators and/or the positions and orientations of the instruments are determined based on one or more signals from optical sensors (e.g., image capture devices). The manipulators or the instruments are equipped with optical fiducials detectable by the optical sensors.

Figure 8B:
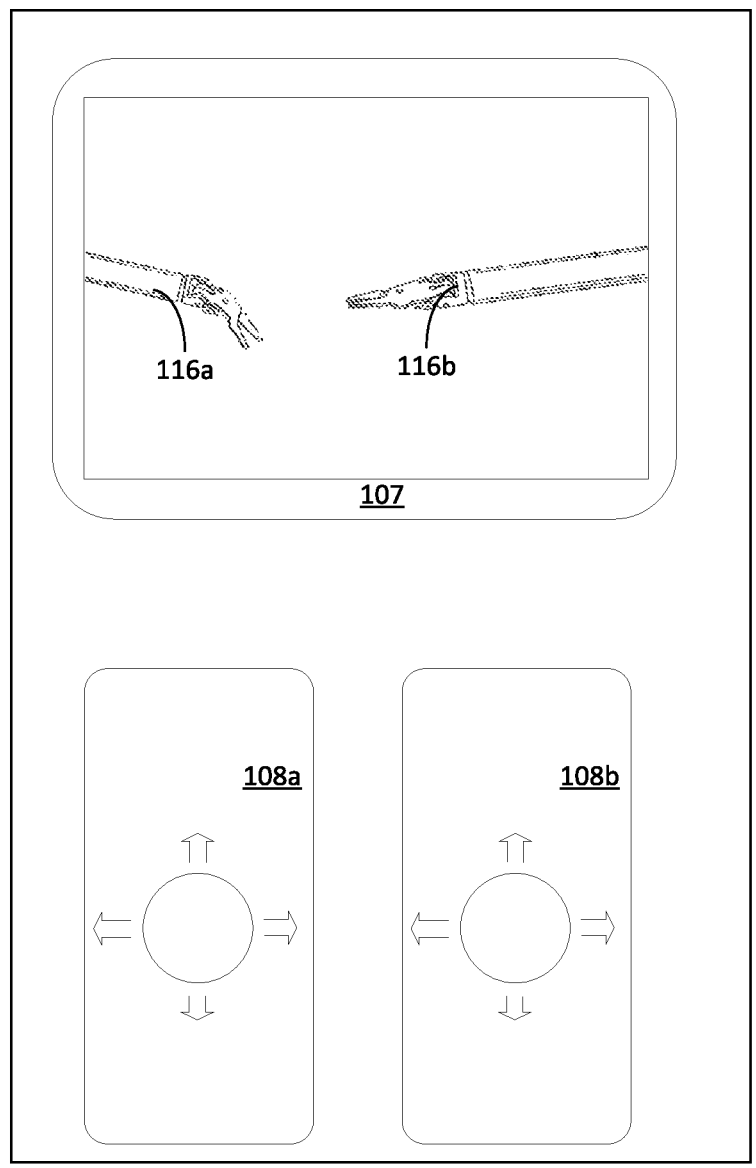
FIG. 8B illustrates, on a left side, a user input system and a display device showing instruments and, on a right side, a top view of manipulators supporting the instruments.

At operation 804, based on the received signals, the controller 110 determines optimal associations between the manipulators of the manipulator system 101 and the user-operable portions of the user input system 106. FIG. 8B diagrammatically depicts relative positions of the display device 107 and the user input devices 108. In this example, the user input devices 108 correspond to the user-operable portions described with respect to FIG. 8A. The representation 122a of the instrument 116a appears on a left side of imagery presented on the display device 107, while the representation 122b of the instrument 116b appears on a right side of the imagery. To provide the operator 104 with intuitive control of the instruments 116a, 116b as the instruments 116a, 116b appear on the display device 107, the controller 110 provides a recommendation to associate the user input device 108a (in the left hand of the operator 104) with the instrument 116a represented on the left side of the imagery. Furthermore, the controller 110 provides a recommendation to associate the user input device 108b (in the right hand of the operator 104) with the instrument 116b represented on the right side of the imagery.

Turning back to FIG. 8A, the controller 110 can determine the relative positions and orientations of the user-operable portions and the manipulators 102a, 102b based on the signals indicative of the poses of these devices. Alternatively, in some implementations, the controller 110 determines the positions and orientations of the user-operable portions relative to the instruments 116a, 116b supported by the manipulators 102a, 102b. The controller 110 can determine relative poses of the instruments 116a, 116b as they would appear to the operator 104 on the display device 107. The controller 110 can determine a recommendation for the associations between the user-operable portions and the manipulators 102a, 102b based on these relative poses. In various implementations, the recommendation may include recommended associations for a subset or all of the user input devices (e.g. 108a, 108b) and a subset or all of the manipulators (102a, 102b). Also, in various implementations, the recommendations may indicate degrees of recommendation for a particular association, such as: a more recommended association between a user input device and a manipulator (e.g. between the user input device 108a and the manipulator holding the instrument 116a), a less recommended association between a user input device and a manipulator (e.g. between the user input device 108a and a manipulator holding an instrument not shown in the imagery), or a not recommended association between a user input device and a manipulator (e.g. the user input device 108a and a manipulator holding the instrument 116b).

In some implementations, the controller 110 does not receive positions and orientations of the user-operable portions for determining the recommendations. The user-operable portions can be configured such that the user-operable portions have fixed positions and orientations relative to one another. In this regard, the controller 110 can provide a recommendation based on the positions and orientations of the manipulators 102a, 102b relative to one another or based on the positions and orientations of the instruments 116a, 116b relative to one another.

After the controller 110 determines the optimal associations, the controller 110 at operation 805 provides a signal to indicate the optimal associations to the operator 104. For example, the controller 110 controls the user output system 202 to provide an appropriate signal to guide the operator 104 to form the optimal associations between the manipulators 102a, 102b and the user-operable portions. For example, the display device 107 can be operated to present a recommendation for the operator to form the optimal associations determined at the operation 804. When a particular user-operable portion is selected for association, the controller 110 can cause the display device 107 to present a recommendation to associate the particular user-operable portion with a recommended manipulator. Turning back to the example of FIG. 8B, when the user input device 108a is selected for association, the virtual selector 121 is presented on the display device 107, and the display device 107 further provides a recommendation to reposition the virtual selector 121 to select the manipulator 102a to associate with the user input device 108a. Similarly, when the user input device 108b is selected for association, the virtual selector 121 is presented on the display device 107, and the display device 107 further provides a recommendation to reposition the virtual selector 121 to select the manipulator 102b to associate with the user input device 108b.

Figure 9:
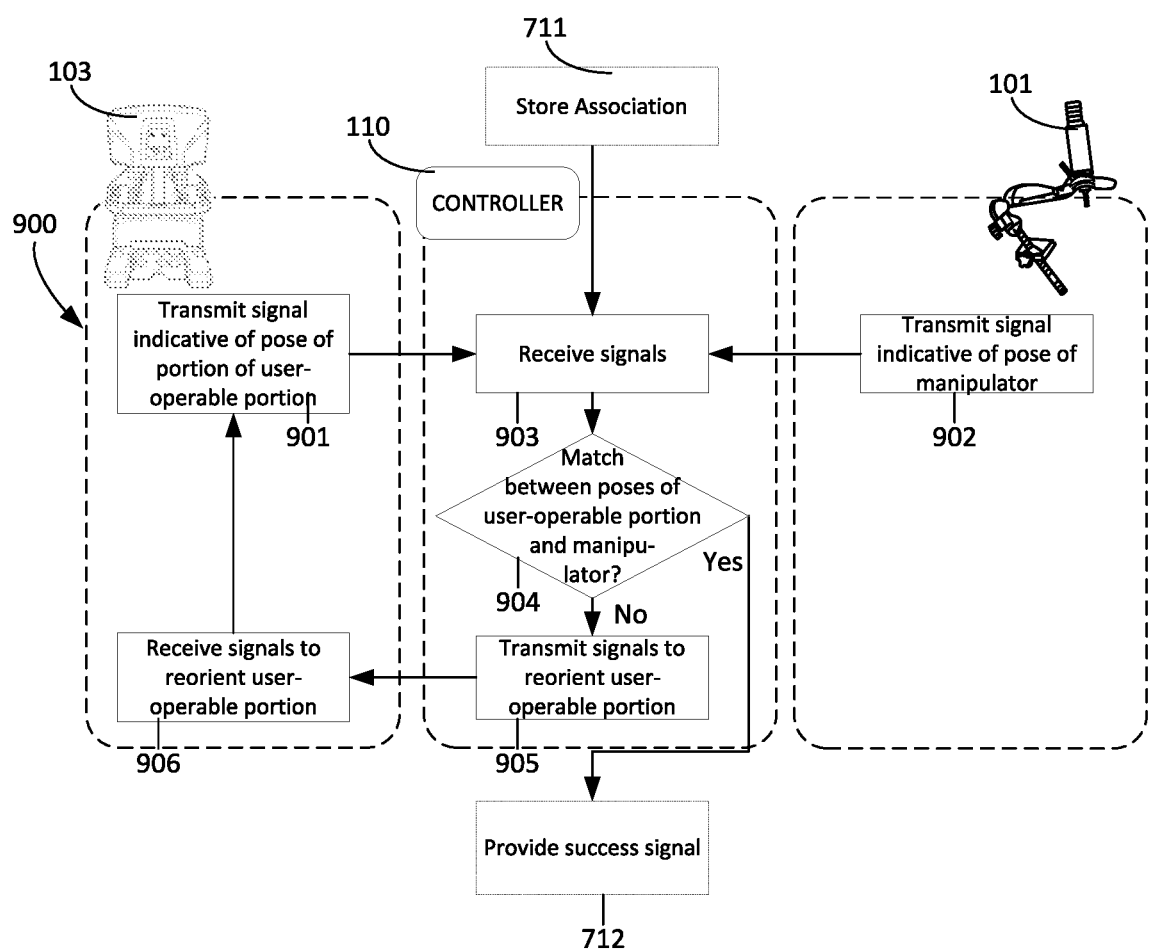
FIG. 9 is a flowchart illustrating a process to reorient user-operable portions of a user input system.

In some implementations, prior to initiating the following mode and after the associations between user-operable portions and manipulators are formed, for each user-operable portion, poses of the user-operable portions and the manipulators can be adjusted to allow for easier operation of the user-operable portions in the following mode. To ensure that the operator 104 can control the manipulator 102 through its full range of motion using the user-operable portion, the portion of the user-operable portion can be reoriented or repositioned. Process 900 of FIG. 9 is performed to achieve this reorienting or repositioning of a portion of a user-operable portion.

At operation 901, the user input system 106 transmits a signal indicative of a pose of a portion of a user-operable portion of the user input system 106. The signal can be indicative of the position and orientation of the user-operable portion relative to the full range of motion of the user-operable portion. For example, the user-operable portion can correspond to a joystick, and a position sensor of the sensor system 200 (shown in FIG. 4) that is coupled to the joystick can generate the signal.

At operation 902, the manipulator system 101 transmits a signal indicative of a pose of a manipulator of the manipulator system 101. Position sensors of the sensor system 200, e.g., encoders, accelerometers, etc., can generate and transmit the signal. At operation 903, the controller 110 receives these signals from the user input system 106 and the manipulator system 101.

Based on these signals, at operation 904, the controller 110 determines whether a pose of the user-operable portion relative to a full range of motion of the user-operable portion matches with a pose of the manipulator relative to a full range of motion of the manipulator. For example, the user-operable portion can have a degree of freedom of motion for controlling yaw motion of the distal end of the manipulator. The controller 110 determines whether the position of the user-operable portion within the full range of motion for this degree of freedom of motion matches with the position of the distal end of the manipulator within the full range of motion for its yaw degree of freedom. The controller 110 similarly compares the position of the portion of the user-operable portion for each of its other degrees of freedom to the position of the manipulator for its other degrees of freedom.

If the poses of the portion of the user-operable portion and the manipulator do not match, the controller 110 at operation 905 transmits signals to reorient the portion of the user-operable portion. At operation 906, the user input system 106 receives the signals. In some cases, the signals cause automatic motion of the portion of the user-operable portion.

For example, the signals drive one or more actuators to move the portion of the user-operable portion. Alternatively, the user input system 106 provides feedback to the operator 104 to reorient or reposition the portion of the user-operable portion. The user input system 106 then at operation 901 transmits another signal indicative of the pose of the portion of the user-operable portion, and the controller 110 determines again whether there is match between the poses of the portion of the user-operable portion and the manipulator.

When the controller 110 determines a match at operation 904, the following mode can be initiated. For example, the success signal can be provided at operation 713 of the process 700, and the following mode can then be initiated.

Further Implementations

A number of implementations have been described, and it is contemplated that various combinations, additions, or modifications may be made. For example, the above implementations may be combined in any appropriate manner. As another example, an implementation may include none, one, or a plurality of any of the following.

Figure 10:
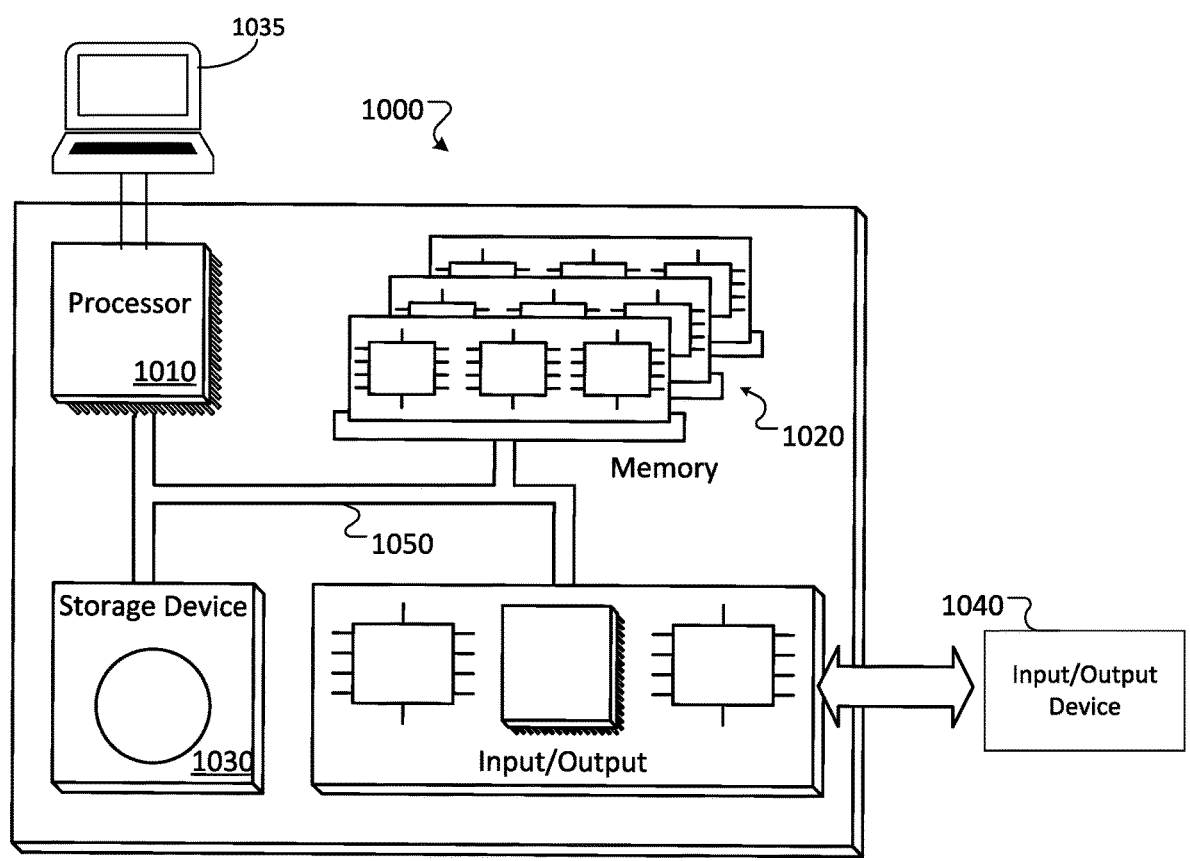
FIG. 10 is a schematic diagram of a computer system.

For example, controllers, processors, and any associated components described herein can be part of a computing system that facilitates control of the systems according to processes and methods described herein. FIG. 10 is a schematic diagram of an example of a computer system 1000 that can be used to implement a controller, e.g., the controller 110 or other controller of the system 100, described in association with any of the computer-implemented methods described herein, e.g., methods including one or more of the processes or operations described with respect to FIGS. 6-9. The system 1000 includes components such as a processor 1010, a memory 1020, a storage device 1030, and an input/output device 1040. The components 1010, 1020, 1030, and 1040 are interconnected using a system bus 1050. The processor 1010 is capable of processing instructions for execution within the system 1000. In some examples, the processor 1010 is a single-threaded processor, while in some cases, the processor 1010 is a multi-threaded processor. The processor 1010 is capable of processing instructions stored in the memory 1020 or on the storage device 1030 to display graphical information for a user interface on the input/output device 1040.

Memory storage for the system 1000 can include the memory 1020 as well as the storage device 1030. The memory 1020 stores information within the system 1000. The information can be used by the processor 1010 in performing processes and methods described herein. In some examples, the memory 1020 is a computer-readable storage medium. The memory 1020 can include volatile memory and/or non-volatile memory. The storage device 1030 is capable of providing mass storage for the system 1000. In general, the storage device 1030 can include any non-transitory tangible media configured to store computer readable instructions. Optionally, the storage device 1030 is a computer-readable medium. Alternatively, the storage device 1030 may be a floppy disk device, a hard disk device, an optical disk device, or a tape device.

In some cases, the processor 1010 is in communication with a remote computing system 1035. The remote computing system 1035 includes, for example, a remote server, a cloud computing device, or other computing device remote from the processor 1010 and its systems. The remote computing system 1035 includes computing resources remote from the environment of the processor 1010, e.g., remote from the surgical environment. In some cases, the remote computing system 1035 includes one or more servers that establish wireless links with the processor 1010. The remote computing system 1035 includes, for example, a portion of a network-accessible computing platform implemented as a computing infrastructure of processors, storage, software, data access, and so forth accessible by the processor 1010.

The system 1000 includes the input/output device 1040. The input/output device 1040 provides input/output operations for the system 1000. In some examples, the input/output device 1040 includes a keyboard, a computer mouse, a pointing device, a voice-activated device, a microphone, a touchscreen, etc. In some cases, the input/output device 1040 includes a display unit for displaying graphical user interfaces.

The features of the methods and systems described in this application can be implemented in digital electronic circuitry, or in computer hardware, firmware, or in combinations of them. The features can be implemented in a computer program product tangibly stored in an information carrier. The information carrier can be, for example, a machine-readable storage device, for execution by a programmable processor. Operations, e.g., of the processes 600, 700, 800, and 900, can be performed by a programmable processor executing a program of instructions to perform the functions described herein by operating on input data and generating output. The described features can be implemented in one or more computer programs that are executable on a programmable system including at least one programmable processor coupled to receive data and instructions from, and to transmit data and instructions to, a data storage system, at least one input device, and at least one output device. A computer program includes a set of instructions that can be used, directly or indirectly, in a computer to perform a certain activity or bring about a certain result. A computer program can be written in any form of programming language, including compiled or interpreted languages. The computer program can be deployed in any form, including as a stand-alone program or as a module, component, subroutine, or other unit suitable for use in a computing environment. The computer program implements, for example, a fast genetic algorithm (FGA).

Generally, a computer will also include, or be operatively coupled to communicate with, one or more mass storage devices for storing data files. Such devices can include magnetic disks, such as internal hard disks and removable disks, magneto-optical disks, and optical disks. Storage devices suitable for storing the computer program instructions and data include all forms of non-volatile memory, including by way of example semiconductor memory devices, such as EPROM, EEPROM, and flash memory devices, magnetic disks such as internal hard disks and removable disks, magneto-optical disks, and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (Cathode Ray Tube) or LCD (Liquid Crystal Display) or OLED (Organic Light Emitting Diodes) monitor for displaying information to the user and one or more input devices by which the user can provide input to the computer, such keyboards, buttons, switches, pedals, computer mice, touchpads, touch screens, joysticks, or trackballs. Alternatively, the computer can have no keyboard, mouse, or monitor attached and can be controlled remotely by another computer. In some implementations, the display device includes a head mounted display device or an augmented reality display device (e.g., augmented reality glasses).

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network. The relationship of client and server arises by virtue of computer programs running on the respective computers and having a client-server relationship to each other.

The processor 1010 carries out instructions related to a computer program. The processor 1010 can include hardware such as logic gates, adders, multipliers and counters. The processor 1010 can further include a separate arithmetic logic unit (ALU) that performs arithmetic and logical operations.

The association process 700 is described as being performed to associate a particular user-operable portion of the user input system 106 with a particular manipulator. In some implementations, the user-operable portion corresponds to a user input device of the user input system 106, such as a joystick. During the process 700, user input devices of the user input system 106 are each associated with a corresponding manipulator of the manipulator system 102. In some implementations, rather than associating a particular user input device with a particular manipulator, a particular user-operable portion of the user input system 106 is associated with a particular manipulator during the association process 700. For example, the user input system 106 can include a user input device having multiple distinct user-operable portions. If the user input device is a touchscreen device, the distinct user-operable portions correspond to user interface elements positioned on different portions of the touchscreen device. In this regard, each user interface element can be associated with a corresponding manipulator during the association process 700.

Figure 11:
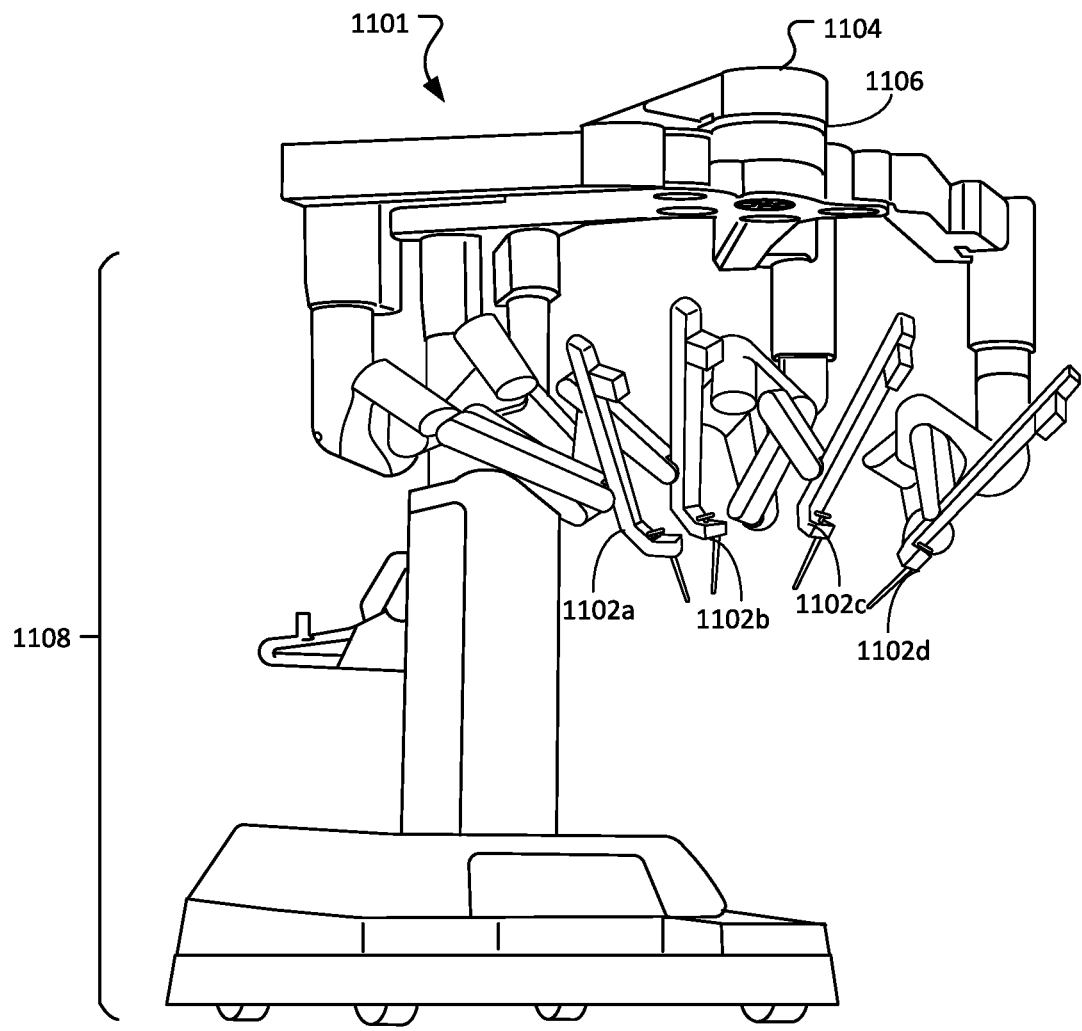
FIG. 11 is a front view of a manipulator system.

While the manipulators 102 are described and shown as being distinct manipulators separately mounted with mounting locations movable relative to each other, e.g., to an operating table, the association processes described herein are also applicable to manipulators that are mounted to a shared base. For example, referring to FIG. 11, a manipulator system 1101 includes manipulators 1102*a*, 1102*b*, 1102*c*, 1102*d* (collectively referred to as manipulators 1102), each of which is mounted to a common base 1104. A joint 1106 can be driven to reorient all of the manipulators 1102. The base 1104 can be mounted to a movable cart portion 1108. The movable cart portion 1108 is, for example, supported above a floor surface by wheels. In this regard, the manipulator system 1101 is easily movable about an environment.

While a single user-operable portion is described as being associated with a single manipulator during the process 700, in some implementations, a set of user-operable portions is associated to a manipulator during an association process. For example, both a left or right joystick and a corresponding left or right foot pedal may be associated to the same manipulator. This enables the operator to control different features of the manipulator, e.g., a position, a velocity, etc., of the manipulator using multiple user-operable portions. In some implementations, instead of having to individually associate each user-operable portion in the set of user-operable portions, the operator can simultaneously associate each user-operable portion of the set of user-operable portions to the manipulator. For example, if the set of user-operable portions includes both a pedal and a joystick, the operator provides the association intent at the operation 705 to move the virtual selector 121 and initiate association of both the pedal and the joystick together to the manipulator.

While the display device 107 shown in FIG. is described as providing visual feedback to the operator 104, in some implementations, other indicator devices are operated to provide a human-perceptible indication indicative of information pertaining to an instrument or pertaining to progress of an association process. For example, indicator devices can provide human-perceptible tactile feedback, aural feedback, or a combination thereof. If the indicator devices provide tactile feedback, the tactile feedback can include vibro-tactile feedback, force feedback, or other forms of feedback associated with a user's sense of touch. The indicator devices can include, for example, a vibration generator. For example, in implementations in which the user input system 106 is manually operable, the indicator devices can be coupled to the user input system 106 and can generate vibrations that serve as haptic feedback for the operator 104 when the operator 104 is manually operating the user input system. If the indicator devices provide aural feedback, the indicator devices include, for example, an audio output device such a speaker. In such cases, the indicator devices can narrate audible feedback to the operator.

While the region 123a shown in FIG. 7B is described as surrounding the portion 124 of the representation 122a of the instrument 116a (corresponding to the end effector of the instrument 116a), in some implementations, the region 123a surround another portion of the representation. In some examples, the region 123a surrounds a portion of the representation 122a corresponding to a particular component of the instrument 116a, such as a pivot of the end effector, a joint of the end effector, a shaft of the instrument 116a, or other portion of the instrument 116a.

The pairing mode can be initiated in response to a particular event. For example, operations 701-703 illustrate a particular example of initiating the pairing mode in response to operation of the user input system 106. In some implementations, the user input device of the user input system 106 that is operated to initiate the pairing mode corresponds to a user input device operable to initiate a clutching mode in which the manipulators can be manually repositioned. In the clutching mode, brake systems of the manipulators are disabled or joints of the manipulators are released so that the manipulators can be manually repositioned by the operator. In some examples, the pairing mode is also initiated when the clutching mode is initiated.

In some implementations, the pairing mode can be initiated in response to events that are not associated with operation of manually operable user input devices. For example, the controller 110 can be configured to initiate the pairing mode when the system 100 is initialized. In some cases, the system 100 includes an audio input system that detects voice commands issued by the operator 104. The operator 104 can utter a voice command, and the controller 110 accordingly initiates the pairing mode. Alternatively or additionally, the pairing mode can be initiated when a new operator accesses and operates the user input system 106.

In some implementations, in the pairing mode, the user-operable portion to be associated in the process 700 is selected by the operator 104 as described herein. In other implementations, the user-operable portion is selected by the controller 110. For example, the controller 110 selects a particular user-operable portion that is in an unassociated state. If the user input system 106 includes multiple user-operable portions in unassociated states, the controller 110 selects a user-operable portion based on relative association priorities of the user-operable portions. For example, the controller 110 by default can start with selecting a leftmost user-operable portion and sequentially select user-operable portions to the right of the leftmost user-operable portion. This selection scheme can be intuitive for the operator 104 and can reduce the number of operator steps required during the process 700.

While the visual feedback shown in FIG. 7B and provided at the operation 703 is described as being indicative of association states of the manipulators, in some implementations, feedback provided at operation 703 is indicative of association states of the user-operable portions. For example, the display device 107 presents graphic indicators indicative of available user-operable portions for association and further presents association state indicators to indicate the association states of the available user-operable portions.

Figure 12:
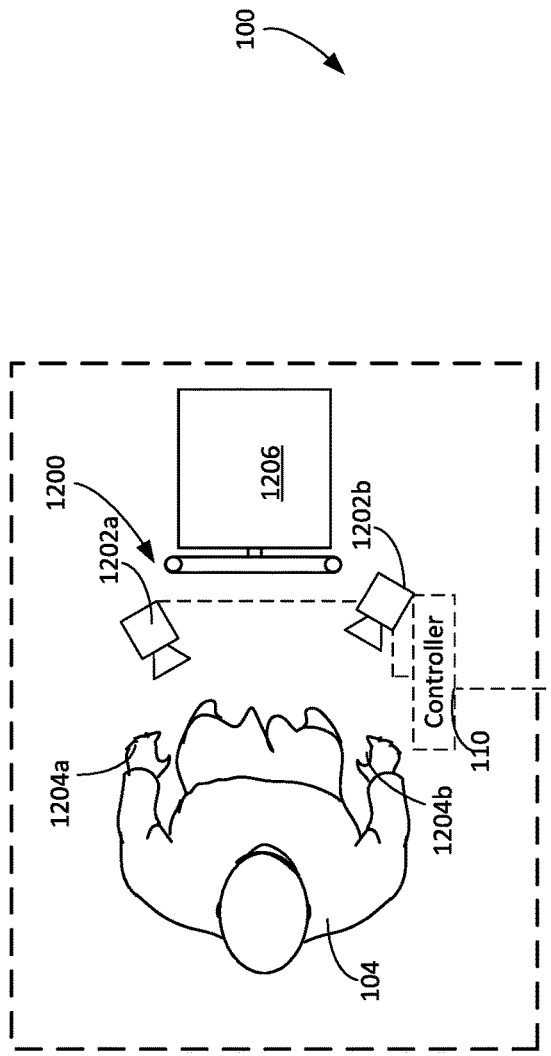
FIG. 12 is a top view of a system including a manipulator and a motion detection system.
Figure 12:
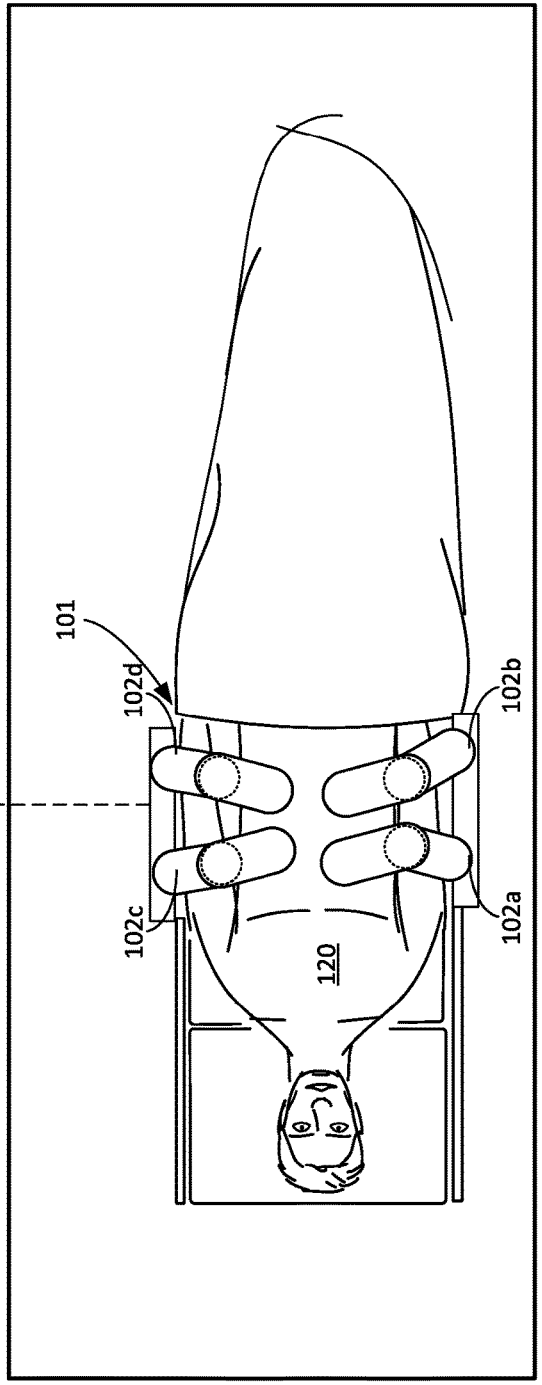

While the processes have been described as being used for association of the user-operable portions with the manipulators 102, in some implementations, the system 100 includes one or more sensors that detect motion and form an association based on the detected motion. For example, the processes described herein are used for association of hands of the operator 104. Referring to FIG. 12, in some implementations, the system 100 includes an optical motion detection system 1200 including optical sensors 1202a, 1202b. The optical motion detection system 1200 is part of the user input system 106 and is operable to move the virtual selector 121 described herein. Rather than including a console 103 with a user output system, the system 100 includes a user output system including a standalone display device 1206 for presenting imagery of the instruments and presenting imagery of the virtual selector 121. In this regard, the display device 1206 is similar to the display device 107 described herein.

The optical sensors 1202a, 1202b can provide a stereoscopic imagery of the operator 104 and can be used to detect motion of the operator 104, in particular, motion of hands 1204a, 1204b of the operator 104. Movements of the hands 1204a, 1204b can be used to control movement of the manipulators 102 in the following mode. For example, the hands 1204a, 1204b are moved in a pattern or sequence in accordance to predefined gestures for controlling the system 100. The predefined gestures can include a gesture for initiating a pairing mode, a gesture for proposing an association between a hand and a manipulator, a gesture for initiating a following mode, or other appropriate gesture to control the system 100. In some implementations, the hands 1204a, 1204b are equipped with gloves detectable by the optical motion detection system 1200.

In addition, in accordance to the association processes described herein, the operator 104 moves hands 1204a, 1204b to control the location of the virtual selector 121. The optical motion detection system 1200 detects the movements of one of the hands 1204a, 1204b, and the controller 110 controls the location of the virtual selector 121 based on the movements of the hand. When the hands 1204a, 1204b are moved in a manner to satisfy the association conditions, the controller 110 forms the associations between the hands

1204a, 1204b and the corresponding manipulators. For example, at operation 705, the operator 104 moves a hand 1204a or a hand 1204b to control the virtual selector 121 to satisfy the association condition. The hands 1204a, 1204b can then be used in the following mode to control motion of the manipulators.

The user input system 106 is described as including, in some implementations, a user-operable portion for controlling the position of the virtual selector 121 that is distinct from the user-operable portions that can be associated to the manipulators. In some examples, the user-operable portion for controlling the position of the virtual selector 121 includes a joystick, a touchscreen, or another manually operable user input device.

Figure 13:
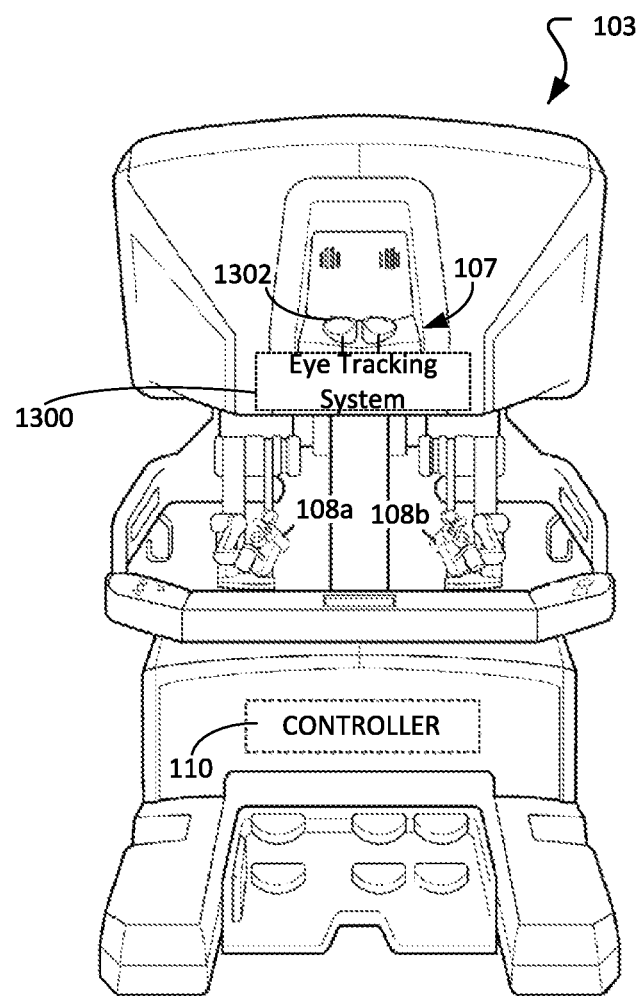
FIG. 13 is a front view of a console including an eye tracking system.

In some examples, referring to FIG. 13, the user-operable portion of the user input system 106 includes an eye tracking system 1300 that detects motion of a gaze of the operator 104 as the operator 104 views the display device 107. In the example shown in FIG. 13, the eye tracking system 1300 is part of the console 103 and detects motion of the eyes of the operator 104 when the eyes are placed on eyepieces 1302 of the console 103. In other examples, the eye tracking system 1300 is part of a non-console input system such as the system 113. During operation, the operator 104 can operate the eye tracking system 1300 by shifting the gaze of the operator 104. When the eyes are positioned on the eyepieces to view the display device 107, the eye tracking system 1300 detects motion of the gaze of the eyes and generates one or more signals indicative of the movement of the gaze. The one or more signals can correspond to the set of signals for controlling the position of the virtual selector 121. The display device 107 can then be operated by the controller 110 based on the set of signals to cause the virtual selector 121 to be moved or repositioned relative to the presented imagery on the display device 107.

As described herein, a manipulator is associated with a user-operable portion so that the manipulator is movable in response to certain operations of the user-operable portion. Thus, in some implementations, the associated user-operable portion can be used for controlling movement of the manipulator. Further, in some implementations, the associated user-operable portion is operable to control other functions of the manipulator or an instrument mounted to the manipulator instead of, or in addition to, controlling movement of the manipulator. In this regard, at operation 603, when the following mode is initiated, the manipulator is not necessarily moved in response to operation of the associated user-operable portion but, rather, receives a signal to perform a particular function or cause the instrument to perform a particular function. For example, in some implementations where the instrument is an image capture device, the associated user-operable portion is operable to control an image capture function of the image capture device, such as a zoom setting, a lighting setting, a shutter speed setting, or other image capture setting. As another example, in some implementations where the instrument is a suction or irrigation device, the associated user-operable portion is operable to control the application of suction or irrigation. In some implementations where the instrument is an image capture device, the associated user input device is operable to control the image capture device to capture imagery. In some implementations where the instrument is a cauterizing device or other energy application device, the associated user input device is operable to control the energy application device to apply energy to tissue.

In some implementations, in the pairing mode, multiple manipulators are associated with a single user-operable portion of the user input system 106. For example, two or more manipulators can be associated with a single one of the user-operable portions 108. When a single user-operable portion is associated with multiple manipulators, the user-operable portion is operable to generate movement of each of the manipulators. For example, in some implementations, if the operator 104 wishes to shift the combined workspace of multiple manipulators or their associated instruments to a different workspace, the operator 104 can operate the user-operable portion to shift each of the manipulators to a vicinity of this different workspace. In some implementations, rather than moving each of the manipulators one-by-one to reach the different workspace, the operator 104 can associate all of the manipulators to be moved, with a single user-operable portion and operate the single user-operable portion to move the plurality of manipulators, as a group, to the vicinity of the different workspace.

As another example, in some implementations, multiple manipulators can be associated with a single user-operable portion of the user-operable portions, and the single user-operable portion controls only one of the manipulators at a time. In some implementations, an operator selects which one of the manipulators is to be controlled by operating the single user-operable portion via an appropriate method, such as depression of a button, turning of a dial, clicking of a pedal, voice commands, etc. In some implementations, the operator operates a button or pedal is used to cycle through manipulators of the manipulators until the one to be controlled becomes active.

Alternatively or additionally, two or more user-operable portions can be associated with a single manipulator. For example, in some implementations, one of the user-operable portions associated with the manipulator is operable to move the manipulator, while the other of the user-operable portions associated with the manipulator is operable to control a non-movement function of the manipulator or a function of an instrument mounted to the manipulator. In some implementations, the two or more associated user-operable portions each is operable to control a different degree of freedom or a different set of degrees of freedom of the manipulator. For example, in some implementations, one of the user-operable portions is manually operable to control a pitch, a yaw, and a roll motion of the manipulator, while the other of the user-operable portions is manually operable to control movement of the instrument relative to the manipulator along the insertion axis or to control actuation of an end effector of the instrument. As yet another example, in some implementations, a plurality of user-operable portions are used to enable a multi-handed input. For example, positions, separation distances, direction of motion, speed of motion of the user-operable portions, relative to each other or a reference, can be used to control the manipulator or an instrument supported by the manipulator.

As a specific example, in an implementation, two user input devices are associated with a single manipulator holding an imaging system such as a camera. An operator holding a user input devices in each hand can control the imaging system with two-handed combination input that simulates manipulation of the work piece relative to the imaging system. For example, in a camera implementation, combined motion of both input devices away from the operator moves the camera away or causes the camera to zoom out, as if the work piece has been pushed away. As another example, in a camera implementation, combined motion of both input devices around a common center rotates the camera field of view, as if the work piece had been rotated. As a further example, in a camera implementation, an increase in the separation distance between the user input devices causes the camera to zoom out, and a decrease in the separation distance between the user input devices causes the camera to zoom in.

In some implementations, the controller 110 is configured to disassociate one or more user input device 108 from one or more manipulators 102 in response to user input or a system event. As an example, the controller 110 may be configured to disassociate an associated pair of manipulator and user input device in response to receiving a signal indicative of a user request to disassociate the first manipulator and the user input device. As another example, the controller may be configured to disassociate all manipulators associated with a user input device, or all user input devices associated with a manipulator, in response to receiving a signal indicative of a user request to disassociate such user input device or such manipulator. In some implementations, the user input system 106 includes disassociating user-operable portions for initiating disassociation of the user-operable portions from the manipulators 102. For example, each of the user input device 108 may comprise disassociating controls or features. As another example, for each of the user-operable portions, a corresponding one of the disassociating user-operable portions can be operated to disassociate a user-operable portion from a manipulator. In addition, in some cases, operation of a disassociating user-operable portion can also initiate the pairing mode.

Accordingly, other implementations are within the scope of the claims.

What is claimed is:

1. A computer-assisted medical system comprising:
   a first manipulator;
   a user input system including an eye tracking system;
   a user output system comprising a display device; and
   a controller configured to execute instructions to perform operations, the operations comprising:
      in a pairing mode and in response to a first set of signals generated by the eye tracking system in response to detecting motion of a gaze of the user, causing a virtual selector shown on the display device to move relative to imagery shown on the display device, wherein the imagery represents a location of a first component of the first manipulator, and wherein the first set of signals are relative to the imagery;
      in the pairing mode, associating the first manipulator with a portion of the user input system based on movement of the virtual selector relative to the represented location of the first component, and
      in a following mode, controlling motion of the first manipulator in accordance with a second set of signals, the second set of signals generated by the user input system in response to user operation of the portion of the user input system.

2. The computer-assisted medical system of claim 1, further comprising a second manipulator, wherein the imagery further represents a location of a second component of the second manipulator, and wherein the operations further comprise:
   in the pairing mode, associating the second manipulator with a portion of the user input system based on movement of the virtual selector relative to the represented location of the second component; and
   in a following mode, after the second manipulator has been associated with the portion of the user input system, controlling motion of the second manipulator in accordance with a third set of signals, the third set of signals generated by the user input system in response to further operation of the portion of the user input system associated with the second manipulator.

3. The computer-assisted medical system of claim 1, wherein the operations further comprise:
   initiating the pairing mode when the computer-assisted medical system is initialized; or
   initiating the pairing mode in response to receiving a signal from the user input system indicative of a request to initiate the pairing mode.

4. The computer-assisted medical system of claim 1, wherein the operations further comprise:
   providing feedback indicative of a proposed association between the portion of the user input system and the first manipulator based on the movement of the virtual selector; and
   associating the portion of the user input system with the first component in response to receiving a signal indicative of a user confirmation of the proposed association.

5. The computer-assisted medical system of claim 1, wherein the operations further comprise:
   causing the user output system to generate a human-perceptible indication of an association state of the first manipulator, the human-perceptible indication including visual feedback, aural feedback, or tactile feedback.

6. The computer-assisted medical system of claim 1, wherein associating the first manipulator with the portion of the user input system comprises:
   associating the first manipulator with the portion of the user input system in response to the virtual selector moving to a first selectable indicator presented by the display device; or
   associating the first manipulator with the portion of the user input system in response to the virtual selector overlapping with a region in the imagery defined by the represented location of the first component.

7. The computer-assisted medical system of claim 1, wherein associating the first manipulator with the portion of the user input system comprises:
   associating the first manipulator with the portion of the user input system in response to the virtual selector being within a predefined distance from the represented location of the first component; or
   associating the first manipulator with the portion of the user input system in response to the virtual selector moving toward the represented location of the first component.

8. The computer-assisted medical system of claim 1, wherein the operations further comprise:
   initiating the following mode after an orientation of the portion of the user input system is aligned with an orientation of a representation of the first component in the imagery.

9. The computer-assisted medical system of claim 8, wherein the operations further comprise:
   generating motion of the portion of the user input system to align the orientation of the portion of the user input system with the orientation of the representation of the first component in the imagery; or
   guiding manual positioning of the portion of the user input system to align the orientation of the portion of the user input system with respect to the orientation of the representation of the first component in the imagery.

10. The computer-assisted medical system of claim 1, wherein:
   the computer-assisted medical system further comprises a second manipulator;

the imagery further represents a location of a second component of the second manipulator; and the operations further comprise: guiding association of the first manipulator with the portion of the user input system based on positions or orientations of representations of the first component and the second component in the imagery.

11. The computer-assisted medical system of claim 1, wherein associating the first manipulator with the portion of the user input system comprises:

associating the first manipulator with the portion of the user input system only if another manipulator of the computer-assisted medical system is not associated with the portion of the user input system; or associating the first manipulator with the portion of the user input system only if the portion of the user input system is in an unassociated state; or associating the first manipulator with the portion of the user input system only if the first manipulator is in an unassociated state.

12. The computer-assisted medical system of claim 1, wherein the operations further comprise:

disassociating the first manipulator with the portion of the user input system in response to receiving a signal indicative of a user request to disassociate the first manipulator or the portion of the user input system.

13. The computer-assisted medical system of claim 1, further comprising a second manipulator, wherein the user input system comprises a plurality of user input devices, wherein the portion of the user input system comprises a first user input device of the plurality of user input devices, and wherein the operations further comprise:

in the pairing mode and in response to a third set of signals generated by the eye tracking system, causing a second virtual selector shown on the display device to move relative to the imagery shown on the display device, wherein the imagery further represents a location of a second component of the second manipulator, in the pairing mode, associating the second manipulator with the second user input device based on movement of the second virtual selector relative to the represented location of the second component, and in the following mode, controlling motion of the second manipulator in accordance with a fourth set of signals, the fourth set of signals generated by the user input system in response to user operation of the portion of the user input system.

14. A method of operating a computer-assisted medical system comprising a first manipulator, the method comprising;

causing a display device to present imagery and a virtual selector, the imagery representing a location of a first component of the first manipulator;

causing the display device to render movement of the virtual selector relative to the imagery in response to a first set of signals generated by an eye tracking system that detects motion of a gaze of a user;

associating, in a pairing mode, the first manipulator with a portion of the user input system based on movement of the virtual selector relative to the represented location of the first component; and controlling, in a following mode, motion of the first component in accordance with a second set of signals generated by the user input system in response to user operation of the portion of the user input system.

15. The method of claim 14, wherein the imagery further represents a location of a second component of a second manipulator of the computer-assisted medical system, and wherein the method further comprises:

in the pairing mode, associating the second manipulator with a portion of the user input system based on movement of the virtual selector relative to the represented location of the second component; and in a following mode, after the second manipulator has been associated with the portion of the user input system, controlling motion of the second manipulator in accordance with a third set of signals, the third set of signals generated by the user input system in response to further operation of the portion of the user input system associated with the second manipulator.

16. The method of claim 14, further comprising:

providing feedback indicative of a proposed association between the portion of the user input system and the first manipulator based on the movement of the virtual selector; and associating the portion of the user input system with the first component in response to receiving a signal indicative of a user confirmation of the proposed association.

17. The method of claim 14, wherein associating the first manipulator with the portion of the user input system comprise:

associating the first manipulator with the portion of the user input system in response to the virtual selector moving to a first selectable indicator presented by the display device; or associating the first manipulator with the portion of the user input system in response to the virtual selector overlapping with a region in the presented imagery defined the represented location of the first component; or associating the first manipulator with the portion of the user input system in response to the virtual selector being within a predefined distance from the represented location of the first component; or associating the first manipulator with the portion of the user input system in response to the virtual selector moving toward the represented location of the first component.

18. The method of claim 14, wherein:

the imagery further represents a location of a second component associated with a second manipulator of the computer-assisted medical system; and the method further comprises: guiding association of the first manipulator with the portion of the user input system based on positions or orientations of representations of the first and second components in the presented imagery.

19. One or more non-transitory computer readable media storing instructions that are executable by a processing device, and upon such execution cause the processing device to perform operations comprising:

causing a display device to present imagery and a virtual selector, the imagery representing a location of a first component associated with a first manipulator of a computer-assisted medical system;

causing the display device to render movement of the virtual selector relative to the imagery in response to a first set of signals generated by an eye tracking system that detects motion of a gaze of a user;

associating, in a pairing mode, the first manipulator with a portion of the user input system based on movement of the virtual selector relative to the represented location of the first component; and controlling, in a following mode, motion of the first component in accordance with a second set of signals generated by the user input system in response to user operation of the portion of the user input system.

20. The one or more non-transitory computer readable media of claim 19, wherein the imagery further represents a location of a second component associated with a second manipulator of the computer-assisted medical system, and wherein the operations further comprise:

guiding association of the first manipulator with the portion of the user input system based on positions or orientations of representations of the first and second components in the presented imagery.

\* \* \* \* \*